(12) United States Patent
Farr et al.

(10) Patent No.: US 8,858,425 B2
(45) Date of Patent: Oct. 14, 2014

(54) DISPOSABLE ENDOSCOPE AND PORTABLE DISPLAY

(75) Inventors: Mina Farr, Palo Alto, CA (US);
Franklin J. Wall, Jr., Vacaville, CA (US); Chris Togami, San Jose, CA (US); Gary D. Sasser, San Jose, CA (US)

(73) Assignee: Vivid Medical, Inc., Palo Alto, CA (US)

( * ) Notice: Subject to any disclaimer, the term of this patent is extended or adjusted under 35 U.S.C. 154(b) by 907 days.

(21) Appl. No.: 12/759,169

(22) Filed: Apr. 13, 2010

(65) Prior Publication Data

US 2010/0198009 A1    Aug. 5, 2010

Related U.S. Application Data

(63) Continuation-in-part of application No. 12/413,457, filed on Mar. 27, 2009, which is a continuation-in-part of application No. 12/111,107, filed on Apr. 28, 2008, now Pat. No. 8,602,971, which is a continuation-in-part of application No. 11/233,684, filed on Sep. 23, 2005, now Pat. No. 8,480,566.

(60) Provisional application No. 61/082,432, filed on Jul. 21, 2008, provisional application No. 60/612,889, filed on Sep. 24, 2004.

(51) Int. Cl.
*A61B 1/04* (2006.01)
*A61B 1/00* (2006.01)

(52) U.S. Cl.
USPC .......................... 600/109; 600/110; 600/132

(58) Field of Classification Search
CPC .... A61B 1/0008; A61B 1/00071; A61B 1/05; A61B 1/00011; A61B 1/00052; A61B 5/0084; A61B 1/051; A61B 1/00004; A61B 1/00006; A61B 1/00009; A61B 1/00018; A61B 1/012; A61B 1/018; A61B 1/0011

USPC .......... 600/109, 110, 132, 160, 153, 112, 129
See application file for complete search history.

(56) References Cited

U.S. PATENT DOCUMENTS 4,000,417 A   12/1976   Adkisson et al.
4,337,761 A    7/1982   Upsher
(Continued)

FOREIGN PATENT DOCUMENTS

JP    H05285154 A    11/1993
JP    H05337073 A    12/1993
(Continued)

OTHER PUBLICATIONS

International Search Report dated Apr. 23, 2012 as received in application No. PCT/US2011/052039.

(Continued)

*Primary Examiner* — Philip R Smith
*Assistant Examiner* — William Chou
(74) *Attorney, Agent, or Firm* — Maschoff Brennan

(57) ABSTRACT

Various embodiments for providing removable, pluggable and disposable opto-electronic modules for illumination and imaging for endoscopy or borescopy are provided for use with portable display devices. Generally, various medical or industrial devices can include one or more solid state or other compact electro-optic illuminating elements located thereon. Additionally, such opto-electronic modules may include illuminating optics, imaging optics, and/or image capture devices. The illuminating elements may have different wavelengths and can be time-synchronized with an image sensor to illuminate an object for imaging or detecting purpose or other conditioning purpose. The removable opto-electronic modules may be plugged onto the exterior surface of another medical device, deployably coupled to the distal end of the device, or otherwise disposed on the device.

25 Claims, 20 Drawing Sheets

(56) References Cited

U.S. PATENT DOCUMENTS

| | | | |
|---|---|---|---|
| 4,437,458 A | 3/1984 | Upsher | |
| 4,473,841 A | 9/1984 | Murakoshi et al. | |
| 4,527,553 A | 7/1985 | Upsher | |
| 4,869,238 A | 9/1989 | Opie et al. | |
| 4,901,708 A | 2/1990 | Lee | |
| 4,974,076 A | 11/1990 | Nakamura et al. | |
| 4,982,729 A | 1/1991 | Wu | |
| 5,025,778 A | 6/1991 | Silverstein et al. | |
| 5,056,163 A | 10/1991 | Chou | |
| 5,062,697 A | 11/1991 | Mitchell | |
| 5,166,787 A | 11/1992 | Irion | |
| 5,203,320 A | 4/1993 | Augustine | |
| 5,261,392 A | 11/1993 | Wu | |
| 5,285,397 A | 2/1994 | Heier et al. | |
| 5,305,121 A | 4/1994 | Moll | |
| 5,381,784 A | 1/1995 | Adair | |
| 5,475,316 A | 12/1995 | Hurley et al. | |
| 5,494,483 A | 2/1996 | Adair | |
| 5,538,497 A | 7/1996 | Hori | |
| 5,614,941 A | 3/1997 | Hines | |
| 5,643,221 A | 7/1997 | Bullard | |
| 5,645,519 A | 7/1997 | Lee et al. | |
| 5,647,840 A | 7/1997 | D'Amelio et al. | |
| 5,653,677 A * | 8/1997 | Okada et al. | 600/112 |
| 5,667,473 A | 9/1997 | Finn et al. | |
| 5,749,830 A | 5/1998 | Kaneko et al. | |
| 5,800,342 A | 9/1998 | Lee et al. | |
| 5,836,867 A * | 11/1998 | Speier et al. | 600/112 |
| 5,840,013 A | 11/1998 | Lee et al. | |
| 5,895,350 A | 4/1999 | Hori | |
| 6,066,090 A | 5/2000 | Yoon | |
| 6,106,457 A | 8/2000 | Perkins et al. | |
| 6,178,346 B1 | 1/2001 | Amundson et al. | |
| 6,203,493 B1 | 3/2001 | Ben Haim | |
| 6,277,064 B1 | 8/2001 | Yoon | |
| 6,352,517 B1 * | 3/2002 | Flock et al. | 600/595 |
| 6,441,958 B1 | 8/2002 | Yeung et al. | |
| 6,461,359 B1 | 10/2002 | Tribus et al. | |
| 6,471,643 B1 | 10/2002 | Henderson | |
| 6,485,413 B1 | 11/2002 | Boppart et al. | |
| 6,525,875 B1 | 2/2003 | Lauer | |
| 6,616,603 B1 | 9/2003 | Fontana | |
| 6,648,816 B2 | 11/2003 | Irion et al. | |
| 6,711,283 B1 | 3/2004 | Soenksen | |
| 6,736,773 B2 | 5/2004 | Wendlandt et al. | |
| 6,762,794 B1 | 7/2004 | Ogino | |
| 6,878,109 B2 | 4/2005 | Yamaki et al. | |
| 6,916,286 B2 | 7/2005 | Kazakevich | |
| 6,986,738 B2 | 1/2006 | Glukhovsky et al. | |
| 7,029,435 B2 * | 4/2006 | Nakao | 600/153 |
| 7,048,685 B2 | 5/2006 | Sakiyama | |
| 7,074,182 B2 | 7/2006 | Rovegno | |
| 7,413,543 B2 * | 8/2008 | Banik et al. | 600/129 |
| 7,435,218 B2 | 10/2008 | Krattiger et al. | |
| 7,442,166 B2 | 10/2008 | Huang et al. | |
| 7,591,783 B2 | 9/2009 | Boulais et al. | |
| 7,819,877 B2 | 10/2010 | Guzman et al. | |
| 7,892,169 B2 | 2/2011 | Gono et al. | |
| 7,951,072 B2 | 5/2011 | Adams et al. | |
| 7,955,255 B2 | 6/2011 | Boulais et al. | |
| 8,212,858 B2 | 7/2012 | Schechterman et al. | |
| 2001/0007051 A1 | 7/2001 | Nakashima | |
| 2002/0001202 A1 | 1/2002 | Williams et al. | |
| 2002/0120181 A1 | 8/2002 | Irion | |
| 2002/0135871 A1 | 9/2002 | Vodyanoy et al. | |
| 2002/0143239 A1 | 10/2002 | Henzler | |
| 2002/0161283 A1 | 10/2002 | Sendai | |
| 2003/0023150 A1 | 1/2003 | Yokoi et al. | |
| 2003/0120130 A1 | 6/2003 | Glukhovsky et al. | |
| 2004/0039242 A1 | 2/2004 | Tolkoff et al. | |
| 2004/0147806 A1 | 7/2004 | Adler | |
| 2004/0196364 A1 | 10/2004 | Takahashi | |
| 2004/0204628 A1 | 10/2004 | Rovegno | |
| 2005/0001899 A1 | 1/2005 | Banju et al. | |
| 2005/0014994 A1 | 1/2005 | Fowler et al. | |
| 2005/0024505 A1 | 2/2005 | Kawachi | |
| 2005/0038321 A1 | 2/2005 | Fujita et al. | |
| 2005/0043586 A1 | 2/2005 | Suzushima | |
| 2005/0043588 A1 | 2/2005 | Tsai | |
| 2005/0059860 A1 | 3/2005 | Matsumoto et al. | |
| 2005/0096502 A1 | 5/2005 | Khalili | |
| 2005/0154262 A1 | 7/2005 | Banik et al. | |
| 2005/0180700 A1 * | 8/2005 | Farr | 385/89 |
| 2005/0182297 A1 | 8/2005 | Gravenstein | |
| 2005/0222499 A1 * | 10/2005 | Banik et al. | 600/132 |
| 2005/0234296 A1 | 10/2005 | Saadat et al. | |
| 2005/0237605 A1 | 10/2005 | Vodyanoy et al. | |
| 2005/0240077 A1 | 10/2005 | Rovegno | |
| 2005/0272975 A1 | 12/2005 | McWeeney et al. | |
| 2006/0018017 A1 | 1/2006 | Takahashi | |
| 2006/0020171 A1 | 1/2006 | Gilreath | |
| 2006/0041193 A1 | 2/2006 | Wright et al. | |
| 2006/0069313 A1 | 3/2006 | Couvillon et al. | |
| 2006/0069314 A1 * | 3/2006 | Farr | 600/179 |
| 2006/0167531 A1 * | 7/2006 | Gertner et al. | 607/86 |
| 2006/0178556 A1 | 8/2006 | Hasser et al. | |
| 2006/0189845 A1 * | 8/2006 | Maahs et al. | 600/146 |
| 2006/0287582 A1 | 12/2006 | Toda | |
| 2007/0015964 A1 | 1/2007 | Eversull et al. | |
| 2007/0058249 A1 | 3/2007 | Hirose et al. | |
| 2007/0073109 A1 | 3/2007 | Irion | |
| 2007/0106117 A1 | 5/2007 | Yokota | |
| 2007/0106121 A1 | 5/2007 | Yokota et al. | |
| 2007/0106122 A1 | 5/2007 | Yokota et al. | |
| 2007/0167702 A1 | 7/2007 | Hasser et al. | |
| 2007/0213590 A1 | 9/2007 | Squicciarini | |
| 2007/0225561 A1 | 9/2007 | Watanabe et al. | |
| 2007/0276183 A1 * | 11/2007 | Melder | 600/112 |
| 2007/0292939 A1 | 12/2007 | Chen | |
| 2008/0045800 A2 | 2/2008 | Farr | |
| 2008/0051632 A1 | 2/2008 | Ito et al. | |
| 2008/0207996 A1 | 8/2008 | Tsai | |
| 2008/0208006 A1 | 8/2008 | Farr | |
| 2009/0099550 A1 | 4/2009 | Carrillo et al. | |
| 2010/0198009 A1 | 8/2010 | Farr et al. | |
| 2010/0234925 A1 * | 9/2010 | Harris et al. | 607/88 |
| 2010/0312059 A1 | 12/2010 | McGrath | |

FOREIGN PATENT DOCUMENTS

| | | |
|---|---|---|
| JP | 11216113 A | 8/1999 |
| JP | 2000245689 A | 9/2000 |
| JP | 2003093399 A | 4/2003 |
| JP | 2003-220023 A | 8/2003 |
| KR | 10-2008-0089579 A | 10/2008 |

OTHER PUBLICATIONS

Written Opinion of the International Searching Authority dated Apr. 23, 2012 as received in application No. PCT/US2011/052039.
U.S. Appl. No. 11/233,684, filed Sep. 23, 2005, Mina Farr.
U.S. Appl. No. 12/111,107, filed Apr. 28, 2008, Farr et al.
U.S. Appl. No. 12/413,457, filed Mar. 27, 2009, Farr et al.
PCT/US2009/04118, filed Apr. 20, 2009, Farr et al.
U.S. Appl. No. 12/771,087, filed Apr. 30, 2010, Farr et al.
International Search Report and Written Opinion dated Oct. 30, 2009 as issued in International Application No. PCT/US2009/041118 filed Apr. 20, 2009.
U.S. App. No. 11/233,684, Jul. 13, 2009, Restriction Requirement.
U.S. Appl. No. 11/233,684, Nov. 12, 2009, Office Action.
U.S. Appl. No. 11/233,684, May 14, 2010, Office Action.
Backman, V., et al., "Polarized Light Scattering Spectroscopy for Quantitative Measurement of Epithelial Cellular Structures in Situ," IEEE Journal of Selected Topics in Quantum Electronics, vol. 5, No. 4, pp. 1019-1026 (1999).
International Search Report and Written Opinion Mailed Apr. 10, 2006 in related PCT application No. PCT-US2005-034793.
International Search Report and Written Opinion Mailed Oct. 30, 2009 in related PCT application No. PCT-US2009-041118.
KR Office Action dated Jul. 30, 2014 as received in Application No. 10-2013-7009566 (English Translation).

* cited by examiner

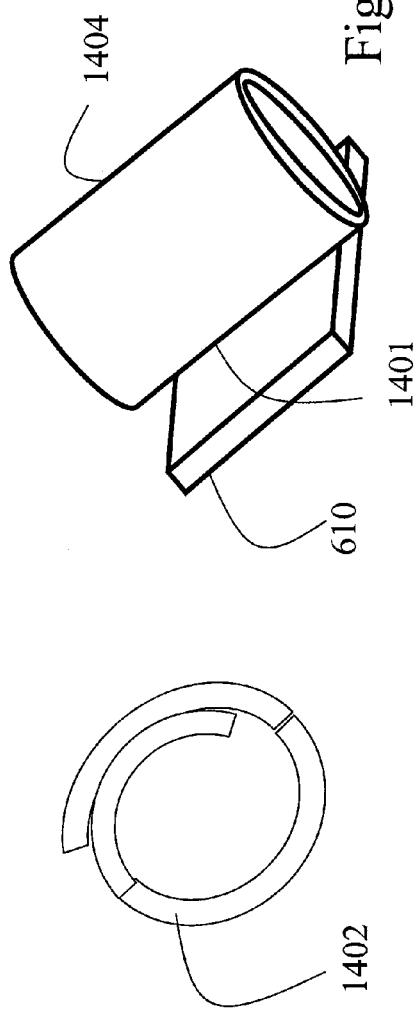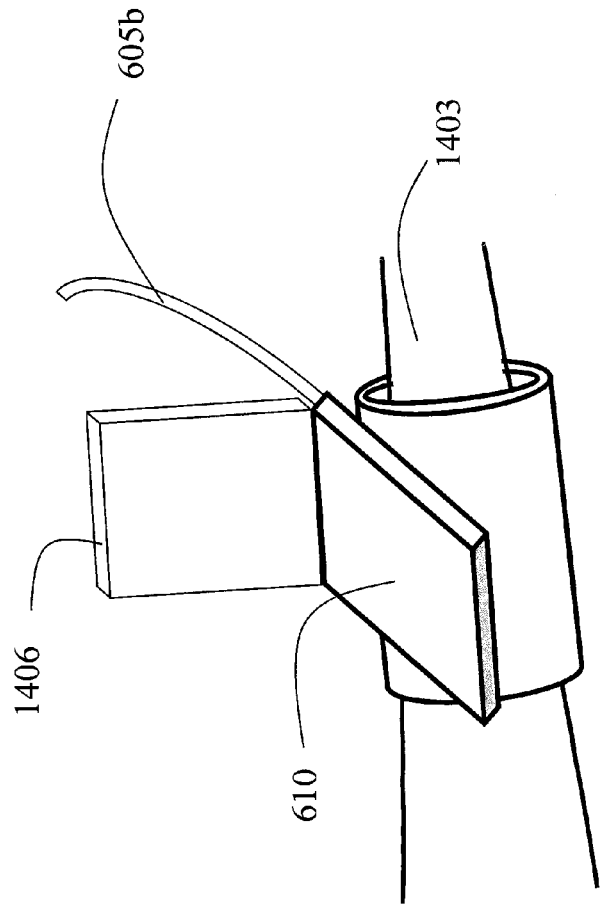

DISPOSABLE ENDOSCOPE AND PORTABLE DISPLAY

CROSS-REFERENCE TO RELATED APPLICATIONS

This patent application is a continuation-in-part of U.S. patent application Ser. No. 12/413,457, field Mar. 27, 2009, and entitled PLUGGABLE VISION MODULE AND PORTABLE DISPLAY FOR ENDOSCOPY, which claims the benefit of U.S. Provisional Patent Application Ser. No. 61/082,432, filed Jul. 21, 2008 and entitled INDIVIDUAL STEREO VIEWER. U.S. patent application Ser. No. 12/413,457 is also a continuation-in-part of U.S. patent application Ser. No. 12/111,107, filed Apr. 28, 2008 and entitled OPTO-ELECTRONIC ILLUMINATION AND VISION MODULE FOR ENDOSOPY, which is a continuation-in-part of U.S. patent application Ser. No. 11/233,684, filed Sep. 23, 2005 and entitled SOLID STATE ILLUMINATION FOR ENDOSCOPY, which claims the benefit of U.S. Provisional Patent Application Ser. No. 60/612,889, filed Sep. 24, 2004 and entitled SOLID STATE ILLUMINATION FOR ENDOSCOPY.

The above-identified patent applications are hereby incorporated herein by reference in their entirety.

BACKGROUND

1. The Field of the Invention

The present invention relates generally to an apparatus for visualization of endoscopic and borescopic fields, in minimally invasive surgical (MIS) procedures, general or diagnostic medical or industrial procedures using endoscopes or borescopes, respectively. More particularly, embodiments of the invention relate to use of pluggable and removable vision systems in endoscopic and borescopic procedures, that are completely disposable, as a means of image capture.

2. The Relevant Technology

Endoscopy is used in both diagnostic and surgical procedures. Currently, MIS procedures, as opposed to open surgical procedures, are routinely done in almost all hospitals. Minimally invasive techniques minimize trauma to the patient by eliminating the need to make large incisions. This both reduces the risk of infection and reduces the patient's hospital stay. Endoscopic procedures in MIS use different types of endoscopes as imaging means, giving the surgeon an inside-the-body view of the surgical site. Specialized endoscopes are named depending on where they are intended to look. Examples include: cystoscope (bladder), nephroscope (kidney), bronchoscope (bronchi), laryngoscope (larynx+the voice box), otoscope (ear), arthroscope (joint), laparoscope (abdomen), gastrointestinal endoscopes, and specialized stereo endoscopes used as laparoscopes or for endoscopic cardiac surgery.

The endoscope may be inserted through a tiny surgical incision to view joints or organs in the chest or abdominal cavity. More often, the endoscope is inserted into a natural body orifice such as the nose, mouth, anus, bladder or vagina. There are three basic types of endoscopes: rigid, semi-rigid, and flexible. The rigid endoscope comes in a variety of diameters and lengths depending on the requirements of the procedure. Typical endoscopic procedures require a large amount of equipment. The main equipment used in conjunction to the visual part of the endoscopic surgery are the endoscope body, fiber optics illumination bundles, illumination light source, light source controller, imaging camera, camera control module, and video display unit.

The laparoscope is a rigid endoscope as illustrated in FIG. 1. It allows for visualization of the abdominopelvic cavities for diagnostic or surgical techniques. The laparoscope is inserted into the peritoneal cavity via a cannula that runs through the abdominal wall. There are many different features of laparoscopes, such as the size and field of vision, which determine the effectiveness of the instrument.

As illustrated in FIG. 1, the basic laparoscope is made up of a long thin tube 101 with an eyepiece 103 at one end for viewing into the patient. Fiber optic light introduced to the endoscope at fiber port 102, and launched into fiber optics 302 (FIG. 3), passes through the endoscope body 101, illuminating the area 304 that is being observed, as illustrated by radiation pattern 306 in FIG. 3. Laparoscopes are characterized by diameter and the direction of view. The direction of view is the angle 107 between the axis 105 of the laparoscope and the center field of view 106, as illustrated in FIG. 1. Typical endoscopes have lengths of approximately 30 cm and diameters in the range of 4 to 10 mm. Laparoscopes consist of two important lenses, the ocular lens at the eyepiece and the objective lens 308 at the distal end of the endoscope 300 in FIG. 3. Other lens sets acting as relay lenses 310 in FIG. 3, are used in-between the objective lens and the eye piece or the CCD camera or image position 312. Imaging rays 314 traverse the length of the scope through all the imaging optics.

The rigid endoscope also comes in different viewing angles: 120 degree or retrograde, for viewing backward; 90 degree and 70 degree for lateral viewing; 30 degree (104 as illustrated in FIG. 1) and 45 degree for forward oblique views; and 0 degree for forward viewing. The angle of the objective lens 308 used is determined by the position of the structure to be viewed.

Other surgical instruments and tools are also inserted into the body, for the operation and specific surgical manipulation by the surgeon. The insertion is done through open tubes provided inside the endoscope body for instrument insertion, such as in gastrointestinal endoscopes, or through separate incisions in the abdominal or chest wall 202, as illustrated in FIG. 2, using cannula 200 (straight or curved stainless steel or plastic tubes which are inserted into a small opening or incision in the skin). The cannula opening at the proximal end 204 outside the body is used to guide different instruments inside the body, where they are exposed to the inside of body at the distal end 206 of the cannula. Cannulas can make a seal at the incision site 208.

In a typical gastrointestinal endoscope, a tool opening is provided at the distal end of the scope, where inserted medical instruments gain access to the body following the scope body.

Endoscopes can be diagnostic, for observation only, or operative, having channels or ports for irrigation, suction, and the insertion of accessory instruments when a surgical procedure is planned. Thus, endoscope bodies also could provide mechanical or electrical control sections, buttons for valves such as a suction valve, a CO2 valve, a water bottle connector, a water feed, a suction port, etc. The common component that all endoscopes must be equipped with is a light guide section for illumination.

An illustration showing typical endoscope optics is shown in FIG. 3. Common imaging sections of the endoscope are an ocular or eyepiece, relay lenses 310 (in the case of rigid scopes), a flexible imaging fiber-optic bundle (in the case of flexible scopes), and an objective lens system 308. Endoscopes are either used as stand alone units, with the surgeon looking into the scope from the ocular or eye piece of the endoscope, or in conjunction with digital cameras, where an image of the surgical site is incident on the image capture device (charge coupled device or CCD) of the camera. Using a display device, the surgeon performs the operation looking at the image on the video monitor.

With recent technology improvements in the field of electronic imaging reducing the size of the image capture device (e.g., CCD), some endoscopes used in MIS and diagnostic procedures are equipped with a high resolution distal end camera system, commonly referred to as Chip on a Stick, one example of which is illustrated in FIG. 4 as camera system 400. These flexible endoscopes use a CCD chip 402 at the distal end of the endoscope directly capturing the image through the objective lens 404, in which case the flexible part 406 of the endoscope body contains only power and communication wires for the CCD camera at the distal tip, rather than imaging optics 408 located in a rigid portion 404 of the endoscope. Light guides 410 running the length of the endoscope are still necessary for this type of electronic scope to provide adequate lighting 412 of the surgical site 414 for imaging purposes.

FIG. 5 depicts a laryngoscope 500 with a handle 504 containing batteries for power, and a curved Macintosh type blade 502, equipped with fiber optic or lamp illumination 506 that is used for manual direct visualization of the larynx used in standard tracheal intubation.

Other, more complicated MIS systems make use of robotic and articulating surgical tools and instruments, and/or provide stereoscopic images of the surgical site for the surgeon, improving the surgeon's dexterity, precision and speed of operation. In these more sophisticated MIS imaging applications more specific types of illumination systems or multiple illuminators are used.

Color CCD cameras use alternate color dies on the individual CCD pixels, to capture color images. Green and red, and green and blue pixels are alternated in rows. This spatial color sampling limits the color resolution of the color CCD cameras, since each pixel is dedicated to capturing a single color in the color image.

3 chip CCD cameras (red CCD chip, blue CCD chip, and green CCD chip) are also used in high resolution applications, where all the pixels in each CCD are dedicated to detecting the single color content of the image. The individual color captured images from the 3 CCDs are then put together electronically, as the multi-color image is reproduced on the viewing display. Three chip CCD cameras are expensive and bulky.

Recent advances in illumination and image capture technology demonstrate the rapid changes that can occur in the capabilities of emerging illumination and imaging systems. For instance, very compact high mega pixel cameras are currently being incorporated widely in cellular phone cameras, whereas just a few years ago this was not possible. It is quite likely that other technological advances in imaging and illumination will occur that can be used in endoscopic medical devices. And, although it may be desirable to incorporate the latest technological advances in illumination and imaging into an endoscopic medical device, this is often impossible without designing and purchasing a brand new replacement of the complete medical device having the improved technology. This complete new solution, however, can be prohibitively expensive especially in the circumstances that the medical providers are under high pressure to reduce cost. Incorporation of the advanced high quality opto-electronics in current and future low cost medical procedures can also be nearly impossible.

Medical diagnostic and treatment procedures are also becoming more available in mobile settings. However, conventional high quality imaging devices are generally not available in convenient packages that are portable and usable without an elaborate setup.

Due to delicate and complicated nature of current endoscope illumination and vision technology, current high performance endoscopes are often limited in sterilization capability, and for the major part not autoclavable. This shortcoming not only limits the life time of these endoscopes to limited number of procedures, but also creates possibility of infection with multiple sterilization and disinfection procedures performed on the current scopes.

BRIEF SUMMARY

These and other limitations are overcome by embodiments of the invention which relate to removable, pluggable, and completely disposable illumination and vision systems that can be coupled to the distal end or housed within the body of a single use removable body, and subsequently attached to various medical devices, including various endoscopic devices used as single use disposable unit, or autoclavable medical access devices used in minimally invasive surgical and other diagnostic procedures. Disposable illumination and vision systems according to some embodiments of the invention include one or more solid state light sources, illumination optics (such as wave guides) and optionally include separate imaging optics and image capture devices, collectively referred to as Opto-Electronic (OE) illumination and vision modules. Removable and pluggable OE illumination and vision modules may additionally include accompanying electronics for process and transfer of the image. Moreover the complete OE vision module and electronics could be housed in a disposable body, where the complete device including the connecting cable can be disposed of after use. Embodiments of the invention also relate to the layouts and functionality of such removable and pluggable vision systems within the body of a disposable endoscope or other disposable medical devices, or within a disposable container in which the removable and pluggable OE illumination and vision modules are housed, and plugged onto a separate non-disposable medical access device or carrier. Embodiments of the invention additionally relate to general layouts of such removable and pluggable vision systems incorporating mechanisms enabling stereoscopic, hyper or varying Field of View (FOV) visual systems.

Embodiments of the invention alternately or additionally include mobile and wearable displays that take advantage of the above embodiments. Some embodiments of mobile and wearable displays can enable minimally invasive surgical and other diagnostic procedures to be performed with minimal setup needs and/or in remote locations, with full connectivity.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

To further clarify the above and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIG. 10b illustrates an articulating flexible medical device being inserted into the pluggable, and disposable OE illumination and vision module of FIG. 10a;

FIGS. 14a-14c illustrate an embodiment of an adjustable, quick mount mechanism for the portable display in FIGS. 6a to 13b, that can be employed to adjustably mount the portable display on a user's arm or wrist;

DETAILED DESCRIPTION

Example embodiments of the invention are directed to disposable solid state opto-electronic vision modules, that can include monochromatic, polychromatic visible, Ultra Violet (UV), and/or Infra Red (IR) solid state light sources such as high power Light Emitting Devices (LEDs) and Laser Diodes as a means of illumination and one or more opto-electronic imaging systems for image capture in diagnostic or surgical endoscopic procedures, or functional borescopic systems.

In various endoscope geometries, it is also possible to install and remove the entire opto-electronic imaging system along with the removable LED illuminator, associated processing electronics, and cable connection for power and control of the device, within the disposable housing, allowing implementation of a removable and pluggable opto-electronic or electro-optic (OE or EO) illumination and/or vision module, as an entirely disposable unit, as described more fully below. The removability and pluggability of such OE vision modules described herein can provide instantly upgradeable illumination and image capture systems without any necessity to replace an entire medical or other functional device still having a remaining useful life.

Advantageously, with the OE vision module removed from the medical device that introduces the pluggable OE vision module into the body, the medical device (access device) can be made autoclavable, which is a highly desirable safety feature not currently available to many endoscopes.

In particular, these removable and pluggable OE illumination and vision modules can be incorporated with a protective disposable cover, at the distal end of a single use disposable or reusable endoscope, borescope, surgical or industrial tools, or be incorporated inside the distal tip end of single use cannulas, or the body of other disposable medical procedure functional devices. They can also be incorporated in a body that is inserted separately, or in conjunction with a lighted or dark scope, into the body. The OE illumination and vision module schemes of the present invention can replace, or can be used in addition to, conventional fiber optic illumination system and other diagnostic devices such as ultrasound imaging used in endoscopy and borescopy.

Figure 6A:
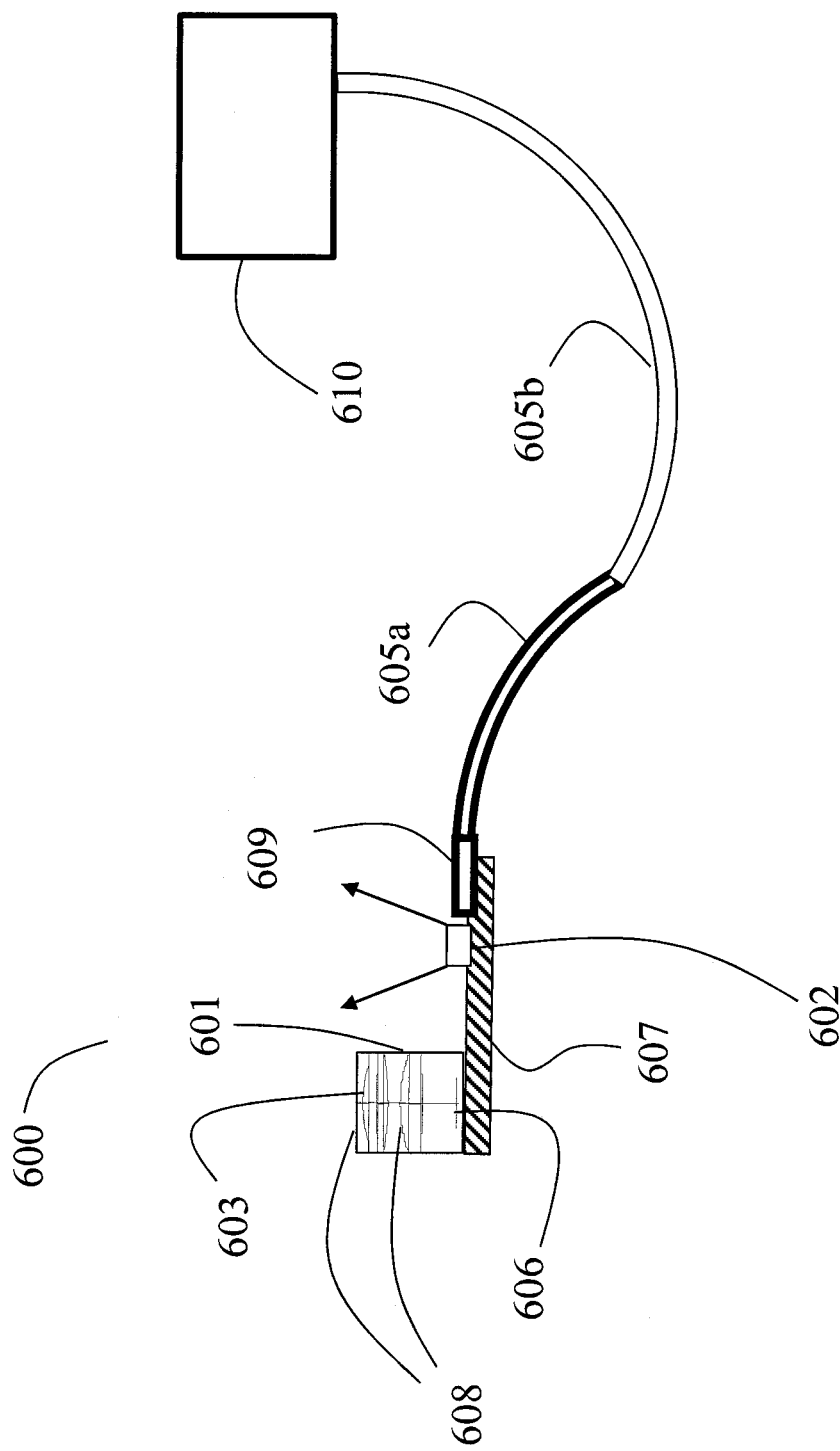
FIGS. 6a to FIG. 6d, illustrate disposable LED illumination and OE vision module comprising a miniature camera unit that can be built into the distal end of a flexible or rigid medical device, and connected to a remote portable display and control unit through flexible electrical circuitry.
Figure 6B:
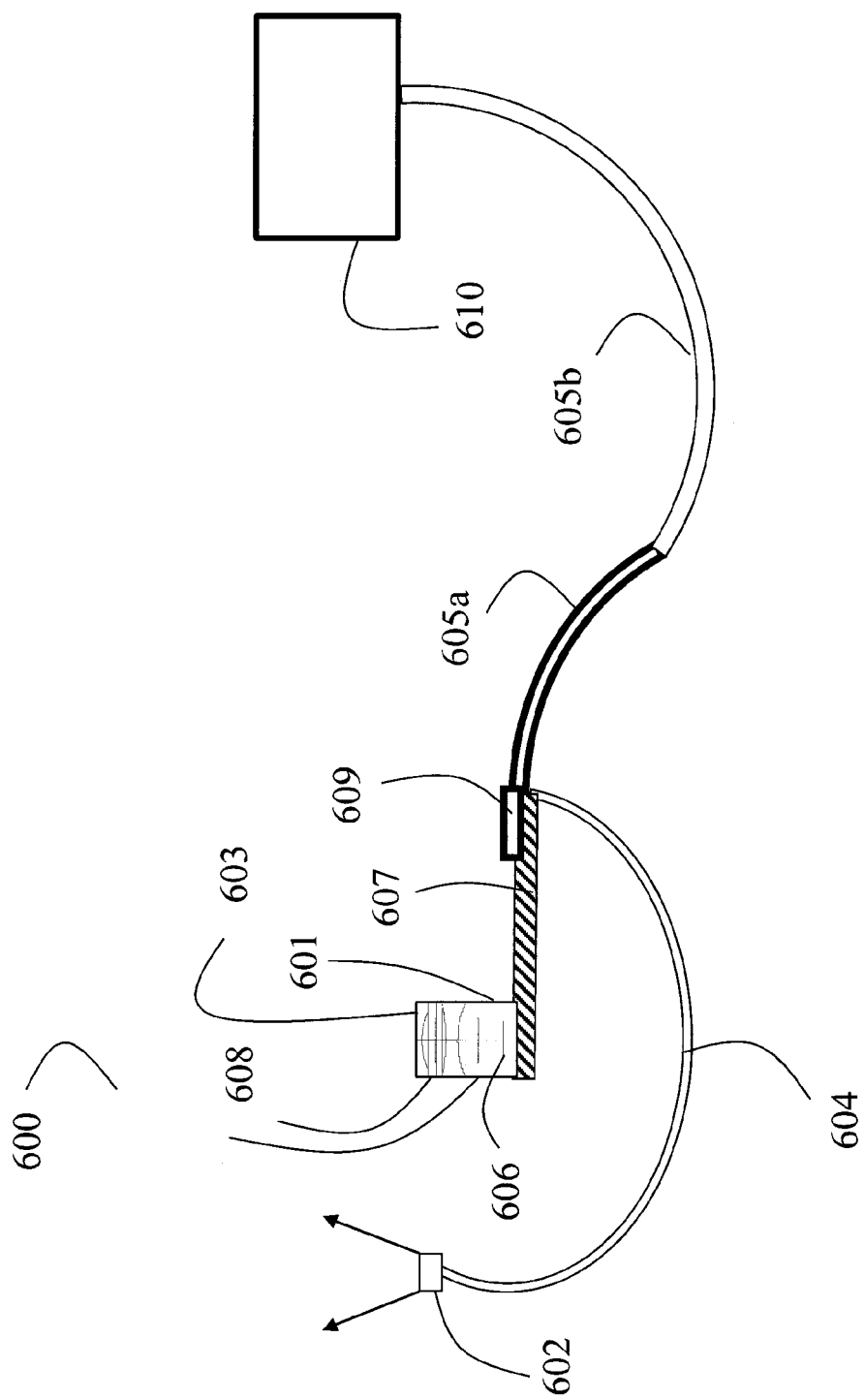
Figure 6C:
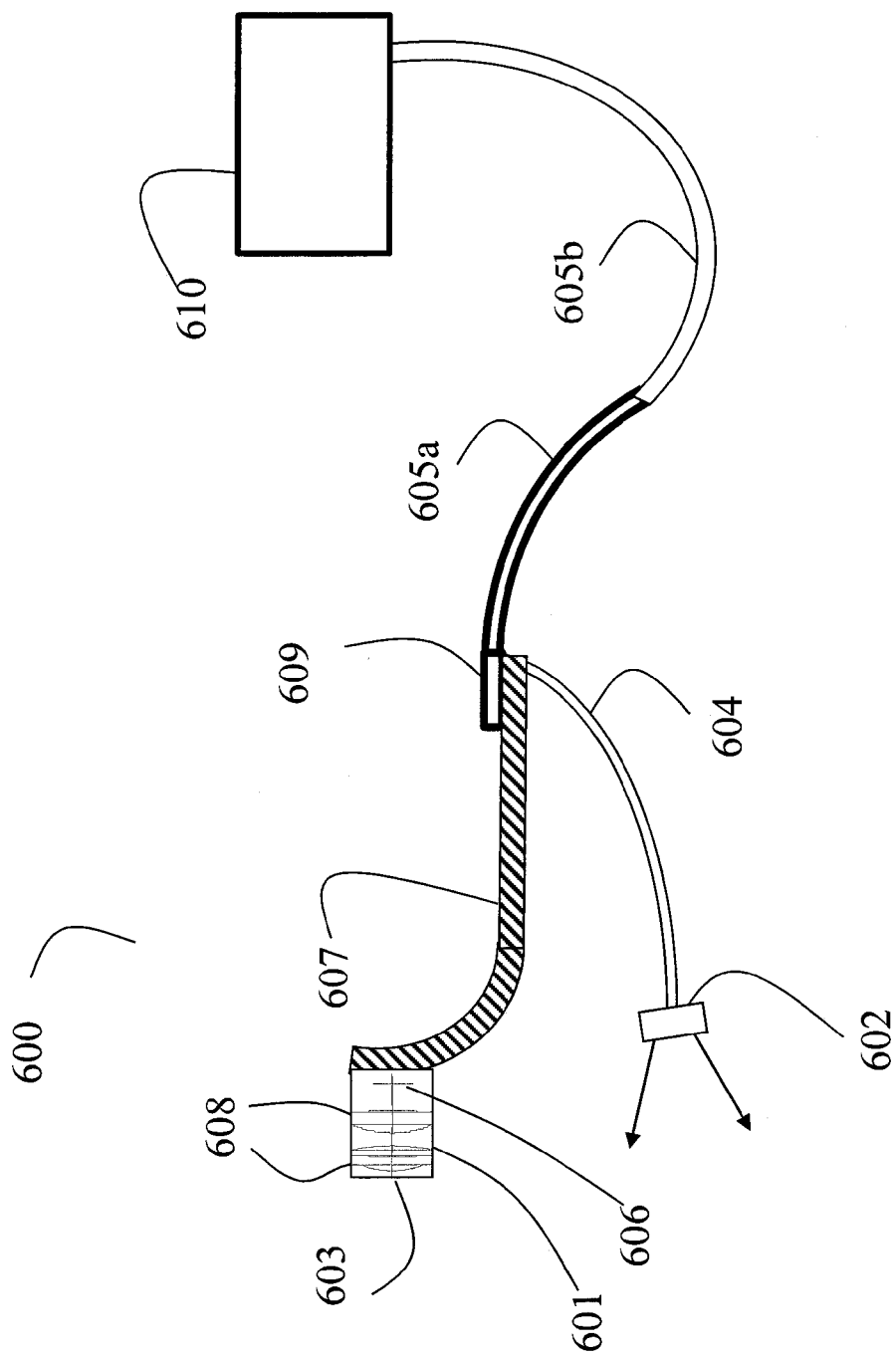
Figure 6D:
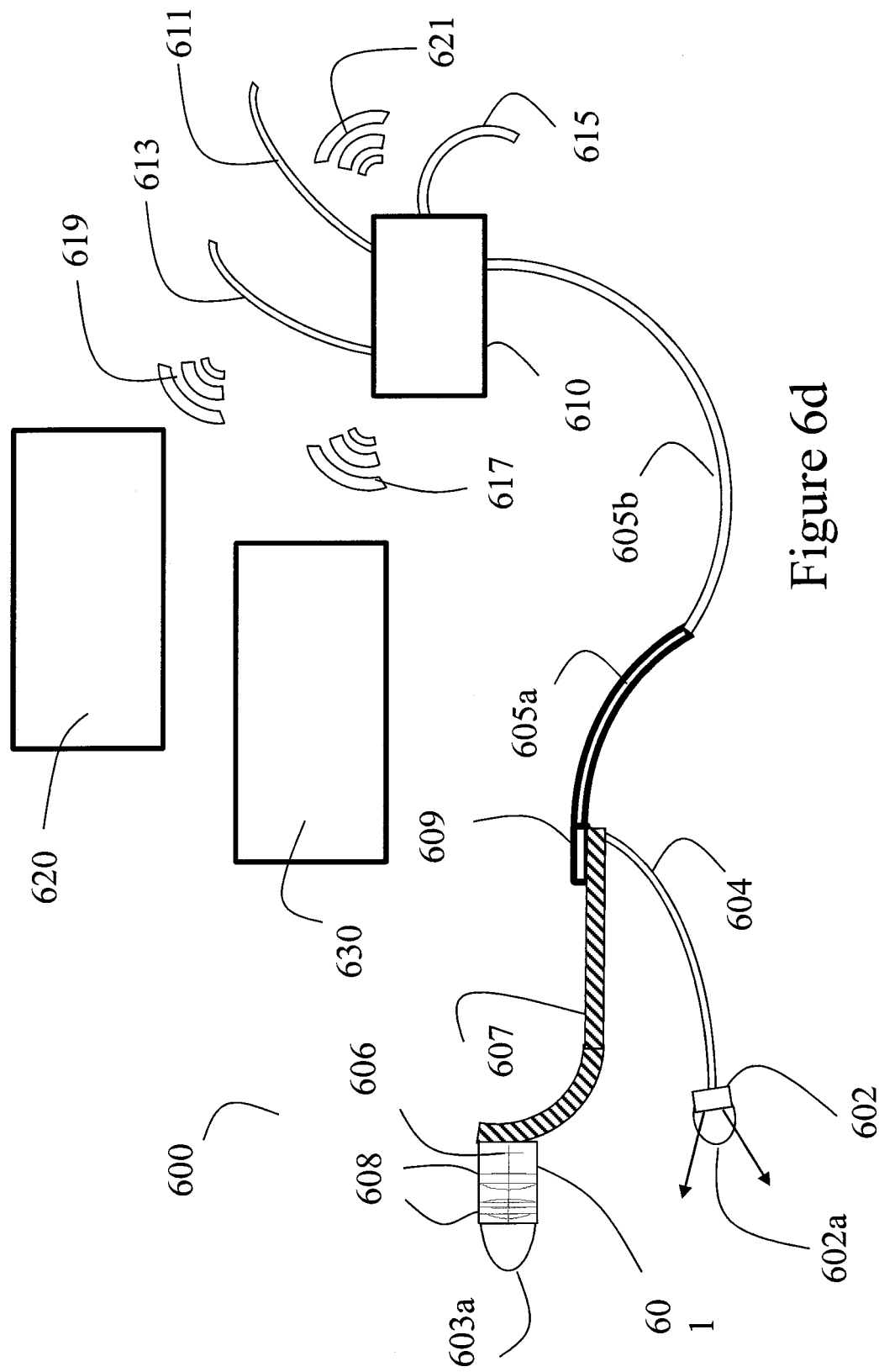

FIGS. 6a to 6c represents OE illumination and vision module 600, comprising a camera and housing 601, within which is disposed one or more imaging lenses 608 and an image sensor 606. A clear optical window 603 is also provided to enclose the imaging lenses 608 and image sensor 606 within the camera housing of 601, mounted on a rigid (FIG. 6a), flexible, or combination electronic processing board 607 (FIGS. 6b-6d). The pluggable OE vision module 600 can be attached to the distal end of a medical device, such as a disposable Chip on the Stick articulating endoscope. Illumination module 602 can be mounted on the same electronics board 607 (FIG. 6a) or have its' own flexible circuitry 604, receiving power from connection 609 and electronic board 607 (FIGS. 6b-6d). Flex circuitry 605a-605b can be used to provide power and control signals to the OE vision module 600 and to transmit imaging signals to a portable control and display unit 610, where part of the cable (605a) can be enclosed along the flexible or rigid body of the disposable endoscope, and part of the cable (605b) can be outside the medical device, where the entire cable can be disposable along with the medical device.

The portable control and display unit 610 generally includes a display screen, a housing, illumination and imaging control electronics, image processing electronics, and/or a power supply, such as a battery. Such compact vision and illumination modules without means of power or control electronics of their own, can be made in a compact and low cost form to make it easily introduced into the body within a disposable housing, by itself or introduced into the body using other standard medical access devices, where they can be removed and disposed of after a single use. Standard low cost and proven digital electronics can be used on the flexible or rigid electronic board 607, to convert the parallel digital video signals from a high resolution digital sensor 606, for example to high speed USB (Universal Serial Bus) video class camera signals (UVC, or USB Video Class format), similar to USB Web cameras, or to send MIPI (Mobile Industry Processor Interface) enabled serialized digital sensor output directly to the Portable Display and Controller 610 with MIPI interface.

In some embodiments, flex circuitry 605a,b communicatively couples the portable control and display unit 610 to the OE vision module(s) 601 to communicate power and control signals, as well as high speed digital video imaging signals between the portable control and display unit 610 and the OE vision module(s) 601. As such, the flex circuitry 605a,b serves as one example of a means for communicatively coupling the portable control and display unit 610 to the OE vision module(s) 601. Additionally, flex circuitry 605a,b further communicatively couples the portable control and display unit 610 to OE illumination modules 602 to communicate power and control signals between the portable control and display unit 610 and the OE illumination modules 602. As such, the flex circuitry 605a,b further serves as an example of a means for communicatively coupling the portable control and display unit 610 to the OE illumination module 602.

For any of the high digital speed communication methods used in cable 605a,b between the display and control device 610 and OE vision and illumination module 600, appropriate connection can be made at the display and control unit, where the entire cable 605a,b can be also disposed of, along with the OE vision and illumination module 600 that is housed in a disposable device housing. Using standard USB communication protocols and connections to the display and control unit, allows the display and control unit be or function as a computing and processing unit such as a UMPC (Ultra Mobile Personal Computer), MID (Mobile Internet Device), a Tablet Computer, or mini PC or a PDA (Personal Digital Assistant) accommodating such USB communication port. Use of such established video communication protocols such as UVC, for example in case of a high speed USB connection, makes the display and control unit to be a device readily available with multiple other connectivity solutions already available in a mobile form. As illustrated in FIG. 6d, other wired connections 611, 613, 615, could be DVI (Digital Video Interface), HDMI (High Definition Multimedia Interface), Ethernet connection, or external power adaptor connection, and wireless interfaces 617, 619, and 621 could be WiFi (wireless Ethernet), Bluetooth, UWB (Ultra Wide Band), IR, or high bandwidth cellular connection.

Other portable or non portable computing and display units, such as 620, and storage devices, such as 630, can be connected wirelessly, or with a wired connection, to the portable display and control unit 610. FIG. 6d also illustrates bulb like protective window 603a and 602a, made of thin molded plastic or glass, that could be placed on the camera housing of camera module 601, and illumination module 602, to act as an optical interface and window between the camera and the illumination module where they are incorporated at the distal tip of medical devices. A single bulb type window could act as a common window for both the illuminator and camera in an alternate embodiment.

Alternatively where a vision system with focusing capability is necessary, compact auto focus mechanism could be also integrated in camera module 601, where certain or all lens elements 608 are to be moved axially with respect to camera sensor 606, with drive and control signals from the control unit 610. Control unit 610 can be programmed to detect best focus of the remote camera module 601 with the imaging data it's provided from the camera and run it as if it's a local camera lens module within the control unit 601.

Removable and pluggable OE illumination and vision modules with protective disposable covers, or implemented in a single use disposable medical device, can enable numerous advantages. For instance, a disposable medical device housing the OE module in a fully sealed sterile cavity can be disposed of after removal of the pluggable OE module from the medical device it's used with, whereupon a new protected and sterile OE module can be plugged onto the medical device housing for subsequent use, thereby eliminating the likelihood of contaminating body cavities in which the disposable medical devices are used.

Some types of removable and pluggable OE vision modules can be plugged onto various designs of single use or reusable medical devices allowing for low cost variations in the medical device design and its functionality. The OE vision and illumination modules covered with a single use protective cover that is fully sealed can be made in various lengths and plugged onto the distal tip of various medical devices, where the protective cover running the length of the inserted medical device can be disposed of after use, and a new protective cover seal on a new OE vision module can be plugged onto the medical device for subsequent use.

Different OE vision and illumination modules, with various functionalities can also be plugged into the same type medical device depending on the procedure to be performed, providing means to choose from a variety of application specific medical vision capability. For instance, white light illumination or multi-spectral visible OE modules can be used for traditional imaging in the visible range.

A pluggable and disposable OE vision and illumination module, with additional deep blue or UV illumination could be used to induce bio-fluorescence inside the body and detect spectral emission from the object, at the same time as the visible imaging, to gain further information regarding the object, such as the tissue type and identifying lesions. An IR illumination can be used in the OE vision and illumination module, to image inside tissue or through scattering substances or fluids, to give additional in depth view. Different UV, visible and IR wavelength illumination with varying penetration depths can be used for depth dependent imaging inside the tissue. Various spectral component captured in 2D images, can be subsequently processed and put together to reconstruct a 3D view of inside the body.

Use of such removable and pluggable OE illumination and vision systems inside a cavity in the body replaces a variety of conventional instruments otherwise needed for the same purpose, such as an external light source, fiber light guides, means of transmitting the light to the desired object, imaging optics, and/or electronic cameras. Further, the removable and pluggable OE systems according to some embodiments of the invention can be used to perform tissue analysis inside the body, thereby eliminating the need for taking tissue for biopsy, and then performing a biopsy on dead tissue. This enables in vivo, in situ tissue analysis without the delay typically required to obtain a biopsy report, and further allows for real-time surgical procedures to be performed instead of possible follow-on surgical procedures after review of biopsy reports.

LED sources can provide illumination in a wide range of the electromagnetic spectrum, from UV, to visible and IR, where the individual LEDs in a specific spectral range can be independently controlled in time and the corresponding images independently processed based on individual captured frames. Each LED spectral component can be independently designed in the LED, or obtained with independent processing of each LED spectrum, via secondary photo-luminescence process on blue or UV LEDs, or using edge or band pass spectral color filters such as multilayer dielectric optical filter coatings. For imaging in the visible region, Red, Green, and Blue LEDs in primary colors can be used with or without other non-primary colors such as amber or cyan where the multiple spectral LEDs together form a white illumination.

By using multiple color LEDs and synchronizing a black and white image capture device to grab the synchronized color component images, the use of color camera chips or high resolution 3 CCD or 3 CMOS imaging devices are eliminated. In this case, a single CCD or CMOS image capture device is used to capture the three or more images in a time synchronized fashion, where each color component image takes advantage of the full image capture device resolution by incorporating all the pixels in each color image component. Simple black and white image capture devices are also cheaper to use, especially compared to 3 chip image capture devices, where in effect the resolution of a synchronized black and white imaging CCD or CMOS using synchronized color illumination provided by the LEDs is equivalent to a same pixel 3 chip image capture device.

Using color synchronized image capture devices also allows the use of much higher resolution image capture devices in chip on the stick cameras where space is limited at the distal tip of the endoscope for the image capture device. A variety of illumination configurations are possible using LED chips, where the uniformity, angle and extent of the illumination are freely controlled by the positioning and design of the LED light sources. Various illumination configurations are disclosed more fully in U.S. patent application Ser. No. 11/233,684.

In current endoscopic imaging systems where a white light illuminator is used, the illumination spectrum is determined by the light source and the optical path the light is transmitted through before reaching the object inside the body. Subsequently, a 3-color image capture device (e.g., a single-chip RGB camera or 3-chip RGB camera) captures the reflected light from the object according to its RGB filter set and image capture device spectral sensitivity. An image display unit in turn displays the captured RGB image according to its own color filters.

Infra Red (IR), Ultraviolet (UV) LEDs, or narrow spectral band VCSELs can be used based on their transmission characteristics in the medium of insertion, such as wavelength dependent penetration depth inside the medium or the effect they have on the object of interest (such as inducing autofluorescence). With an endoscope equipped with a full range of LED wavelengths, or a specific range of illumination wavelength, it is possible to obtain a full spectral image of the object by turning the various LEDs on and off at specified times, and in a controlled spectral range depending on application, while a time synchronized imaging process captures various spectral images based on the illumination at the time of capture. The LEDs can be distributed illuminators used with fixed image capture devices on the scope, introduced within the body of the disposable medical device as part of an OE vision module, or independently introduced inside the body with or without other medical devices.

LED illumination systems or removable and pluggable OE illumination and vision modules are modular, where one or multiple OE modules can be inserted into the body independent of one another, via separate medical device bodies, at the distal end of an disposable endoscope, or incorporated at convenient and efficient locations on surgical tool tips or disposable cannulas, or other single use medical access devices such as disposable catheters, providing an always sterile illumination and visualization of site inside the body. These single use medical devices incorporating the OE illumination and vision system could be battery operated by the portable display and control unit 610, or take power through the medical device that is plugged onto externally.

Figure 1:
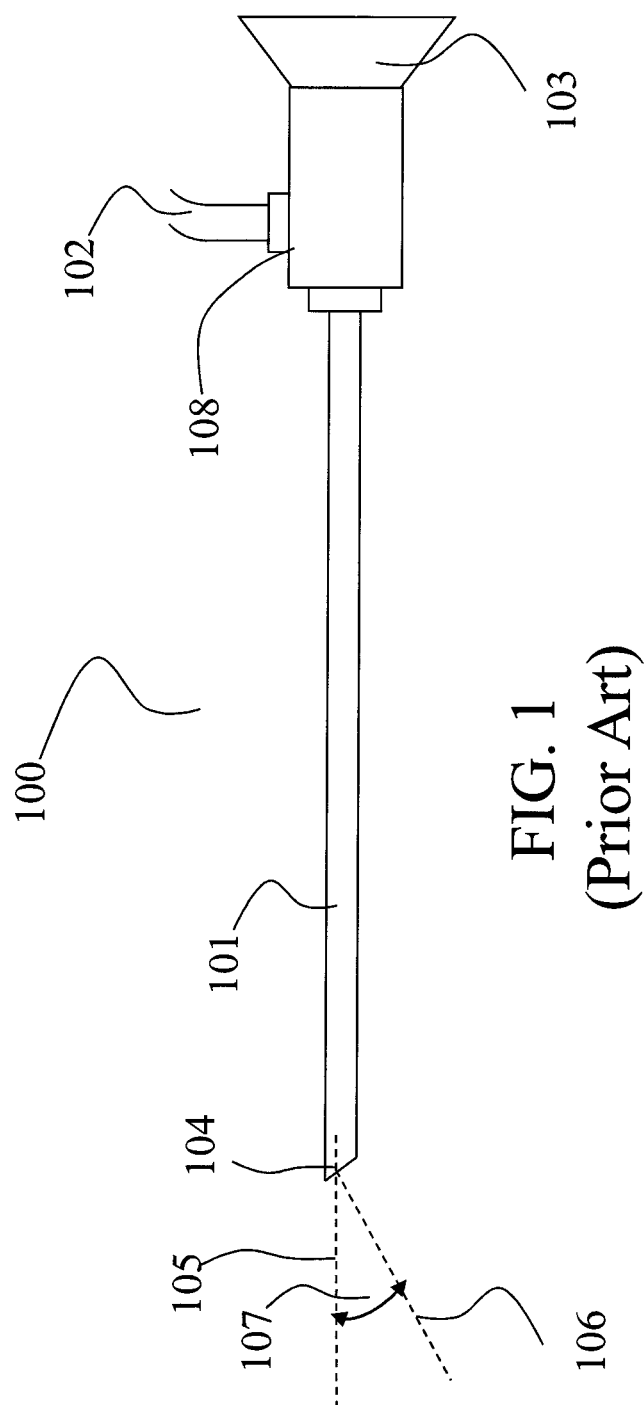
FIG. 1 illustrates a typical angled endoscope, with fiber optic light port for illumination, and an eye piece for viewing.
Figure 2:
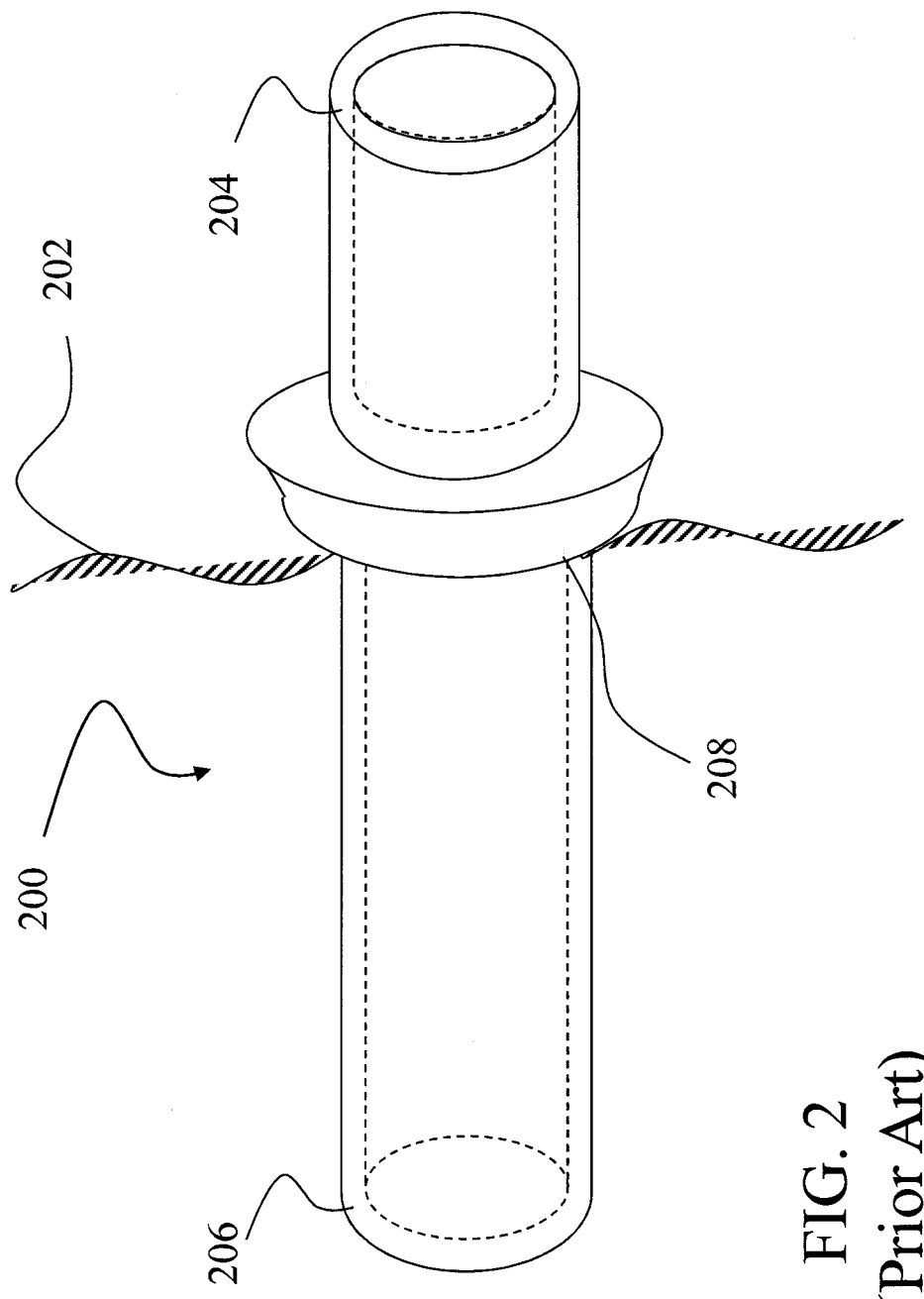
FIG. 2 illustrates a cannula inserted into a body cavity.
Figure 3:
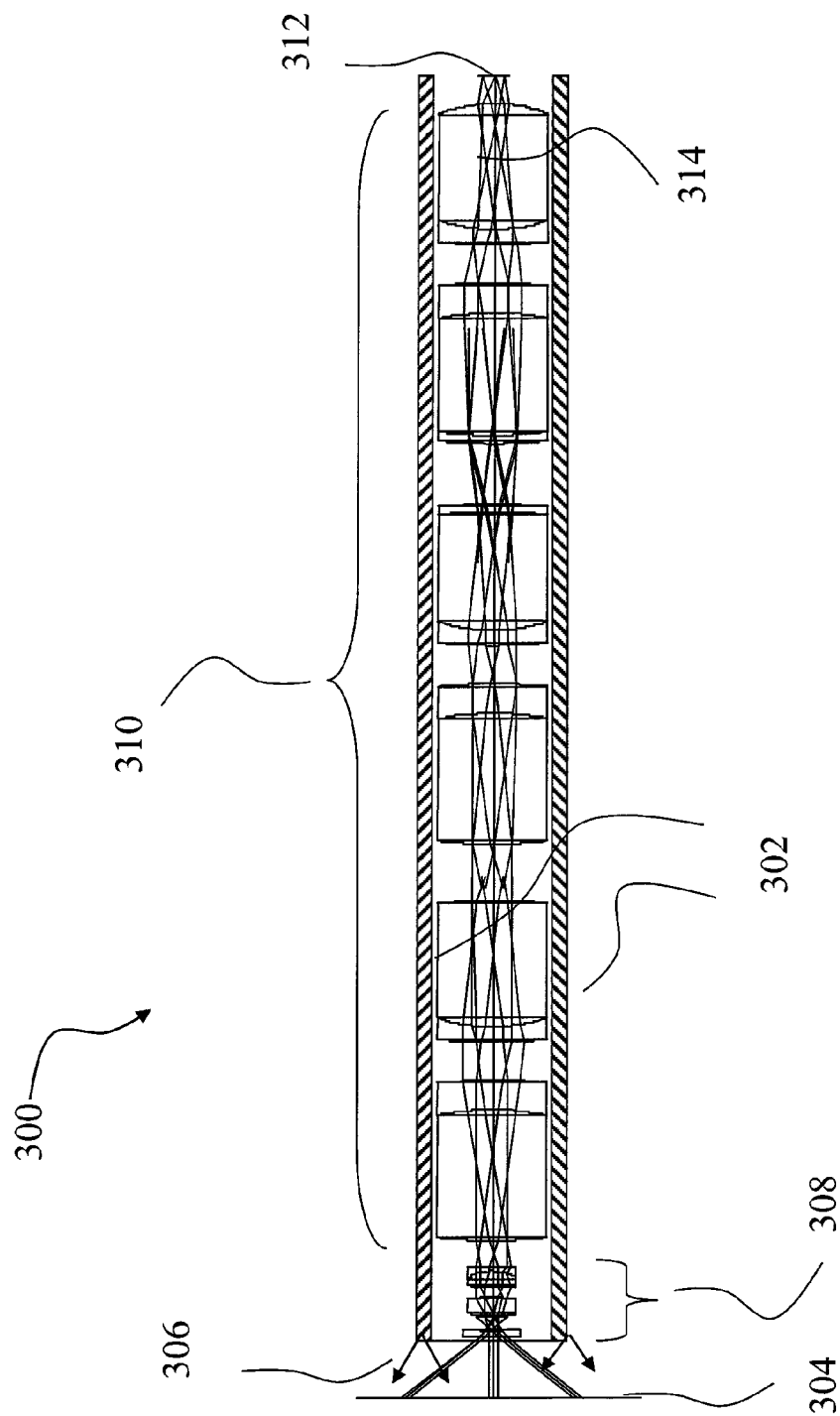
FIG. 3 illustrates a cross-sectional view of a typical zero degree, rigid endoscope with associated terrain for relay of the image through the length of the endoscope.
Figure 4:
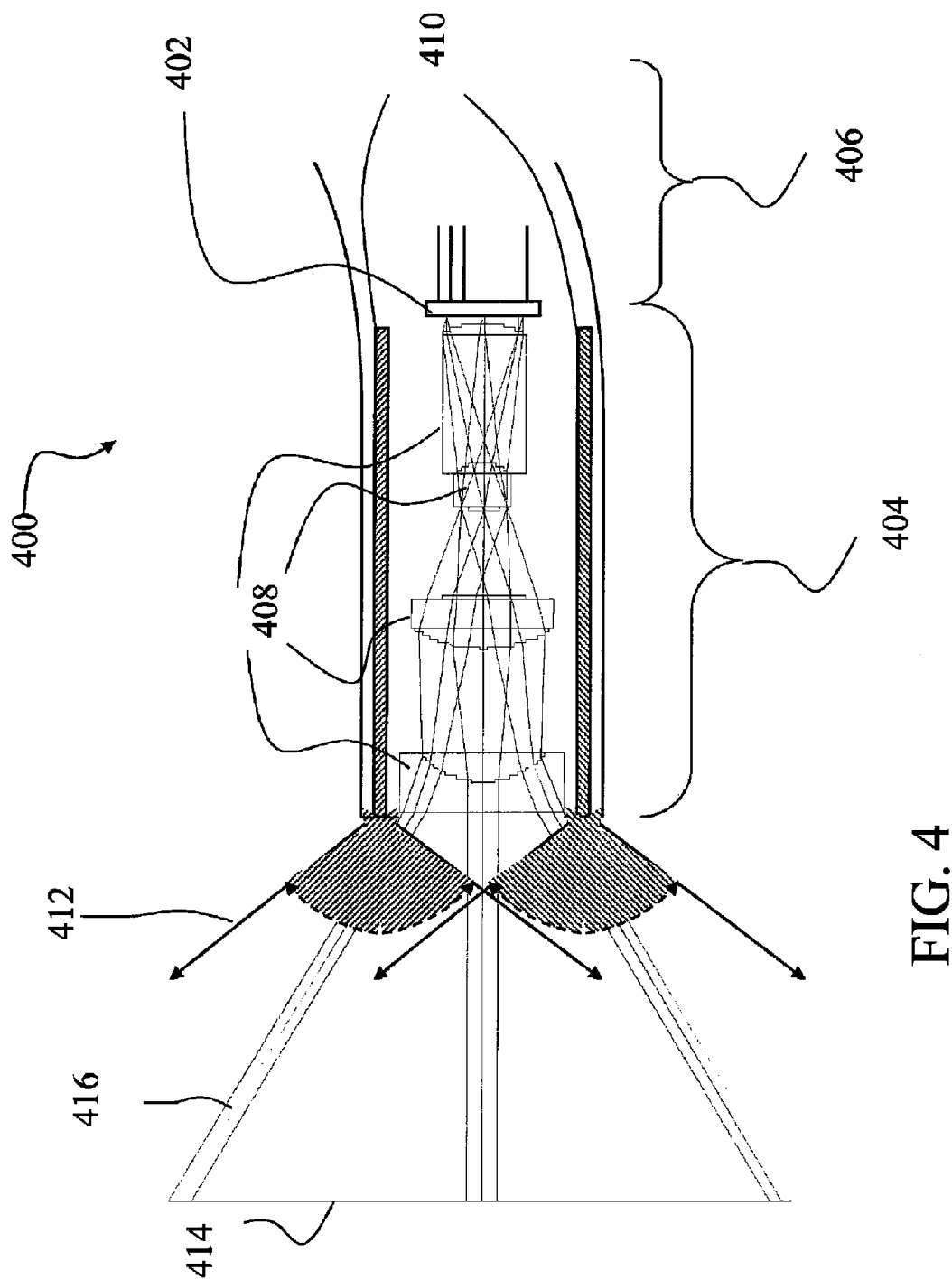
FIG. 4 illustrates a cross-sectional view of a zero degree typical flexible endoscope body (Chip on the Stick) with fiber optics illumination.
Figure 5:
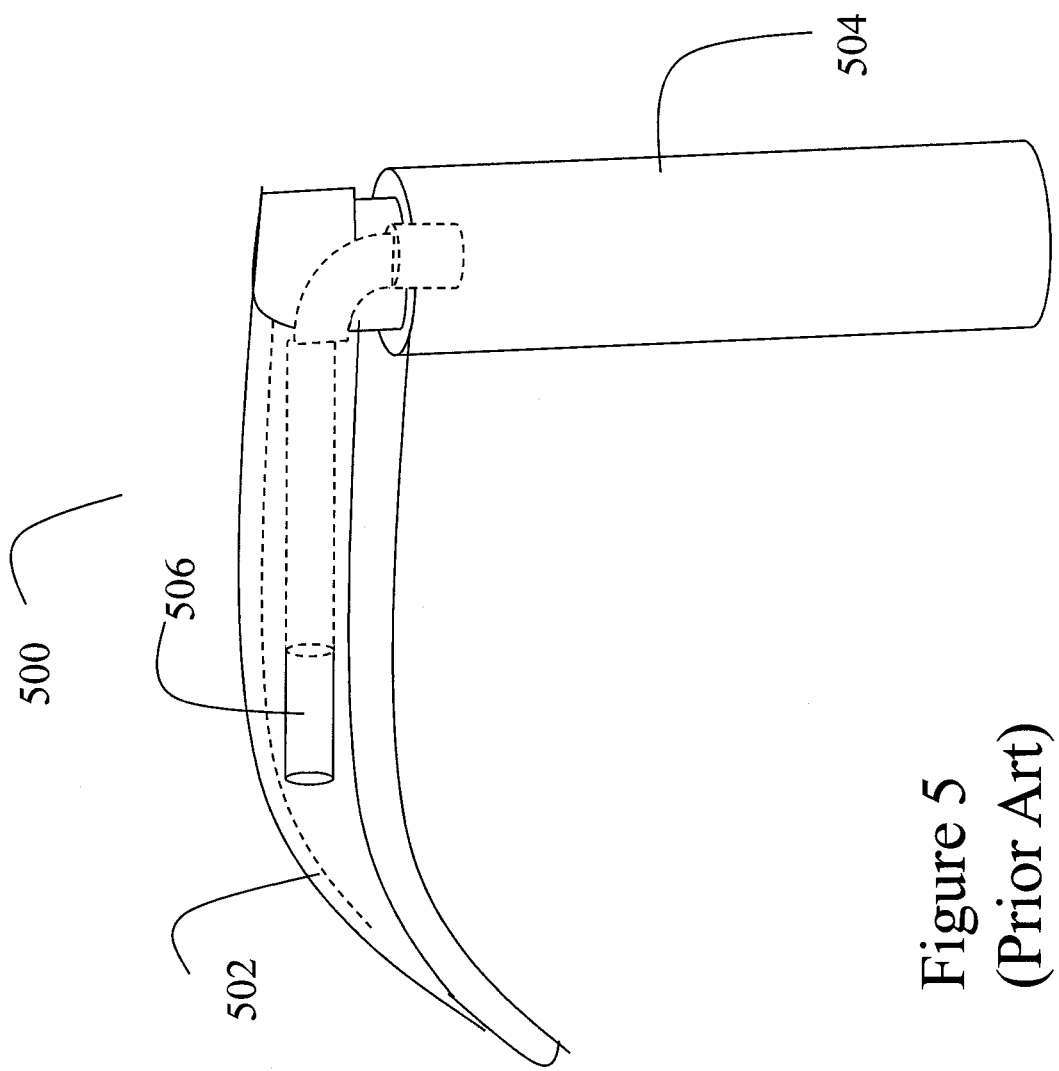
FIG. 5 illustrates a direct laryngoscope with attached Macintosh laryngoscope blade, equipped with a miniature lamp or fiber optic illumination for manual visualization of the larynx.
Figure 7A:
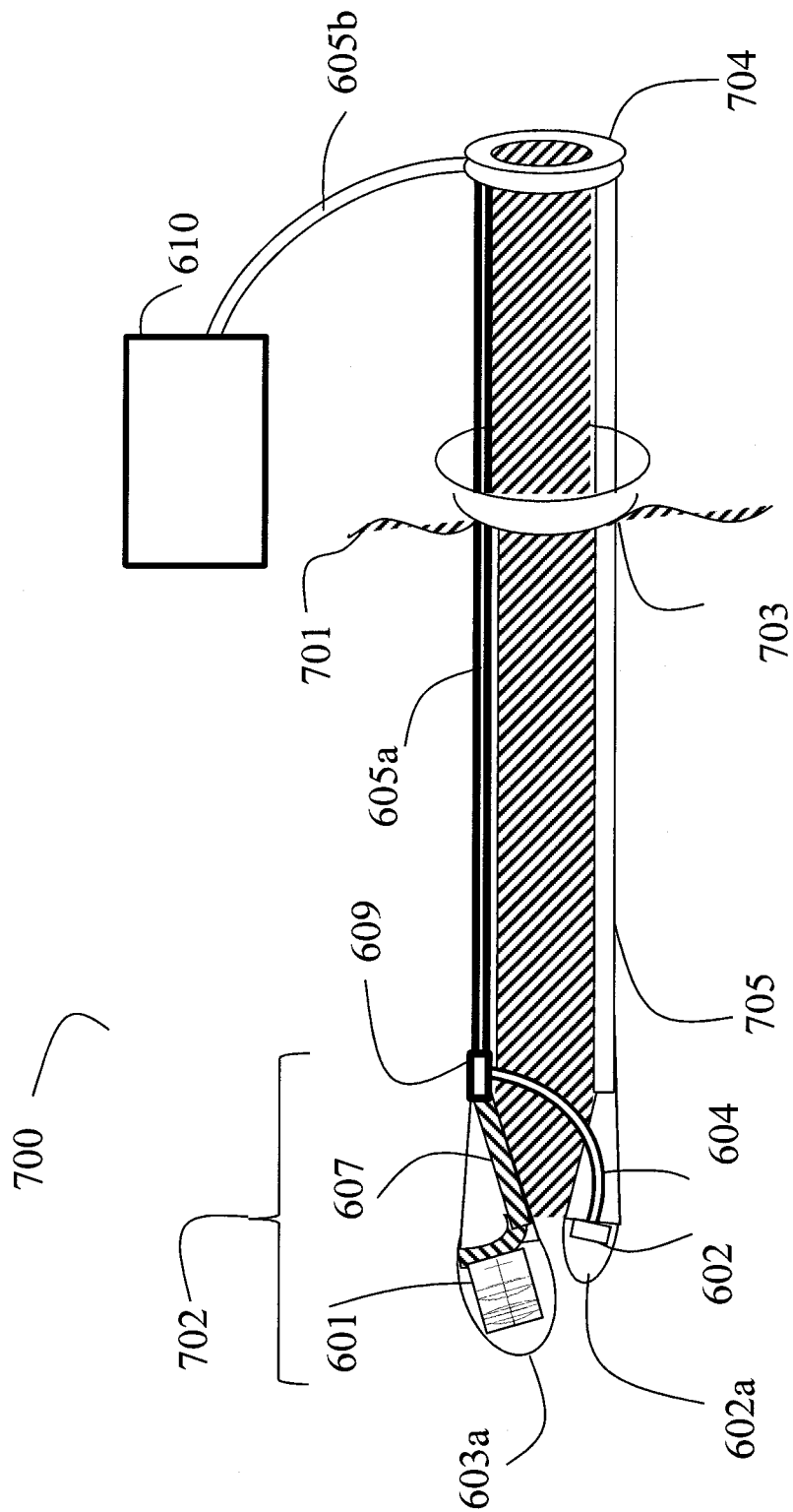
FIGS. 7a and 7b illustrate one example LED illumination and OE vision module (FIG. 6d) incorporated at the expanding distal tip of a disposable cannula.
Figure 7B:
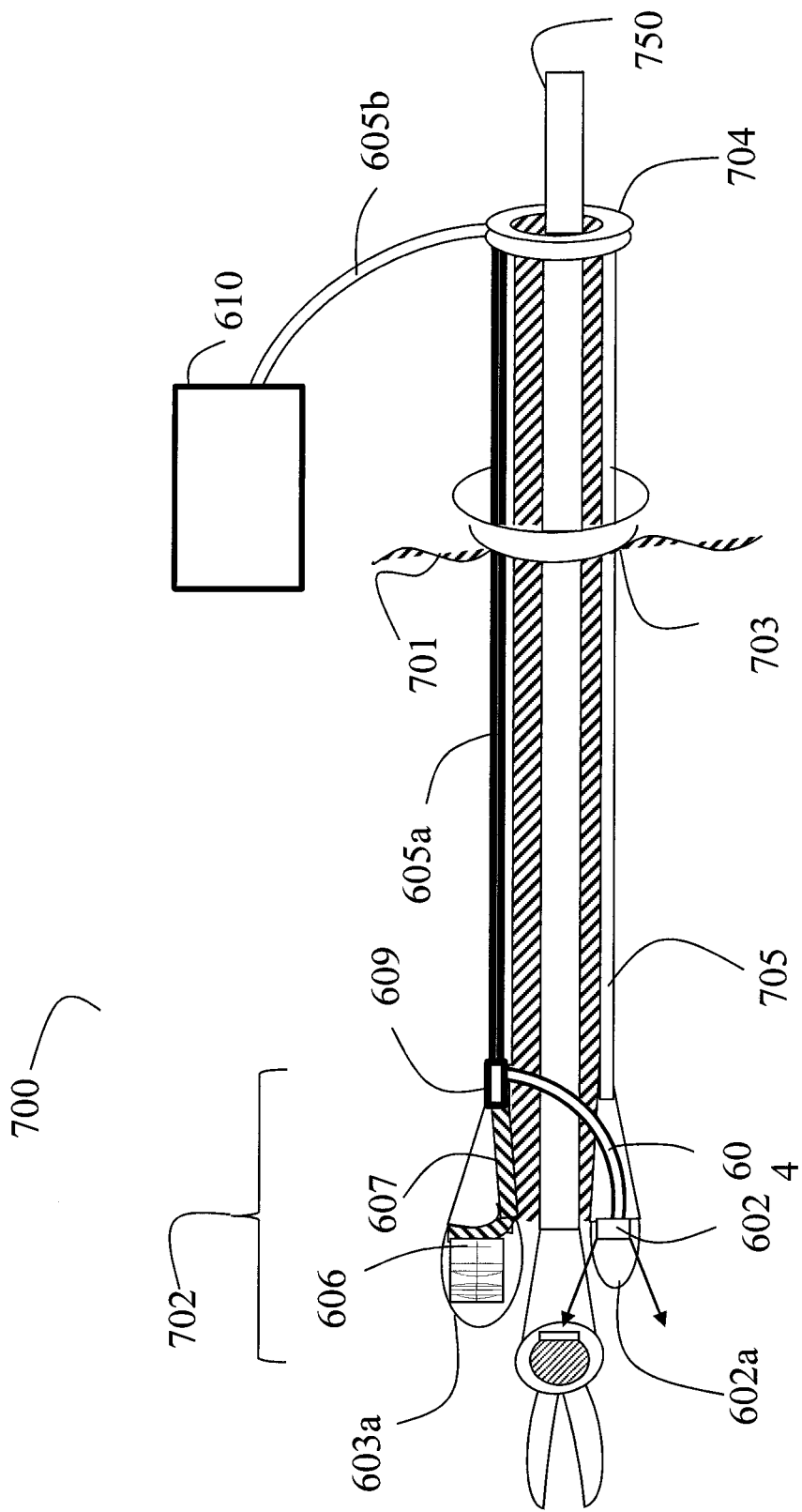

One embodiment of an OE illumination and vision module at the distal tip of a disposable cannula 700 is illustrated in FIGS. 7*a* and 7*b*. Cannula 700 is inserted through the skin 701, at an opening or incision 703. In this example embodiment, the distal tip 702 of the cannula 700 is illuminated by white or color LEDs in illuminator 602 of FIG. 6*d* mounted at the distal end 702 of a cannula, similar to the device in FIG. 2. In addition, the OE vision module 601 of FIG. 6*d* is also mounted at the distal end 702 of the disposable cannula 700. The distal end 702 of the cannula 700 is made flexible in such a way that after insertion into the body through the incision 703, which can be made with or without the aid of a trocar, the distal tip 702 of the cannula can be expanded radially.

Further, as shown in FIG. 7*b*, a surgical tool 750 can be inserted through the disposable cannula 700 after the distal end 702 has been inserted inside the body, and as it is radially deployed. Electrical power to the LEDs 602 and OE vision module 601 is provided by the flexible electrical lines 605*a* that run along the disposable cannula body 705, from the electrical connection 609, of the flexible board 607 and flexible power line 604 connecting to illuminator 602, to the proximal opening 704 of the cannula 700. Outside the body, the flexible electrical cable 605*b* transfers power and control signals to the OE illumination and vision module sensor 606 and illuminator 602, at the distal tip of the disposable cannula 700, from a portable control and display unit 610, while providing the digital imaging data from the camera sensor 606, serialized by for example a USB bridge on the electronic board 607, to the USB Host port of the portable control and display 610.

Figure 8:
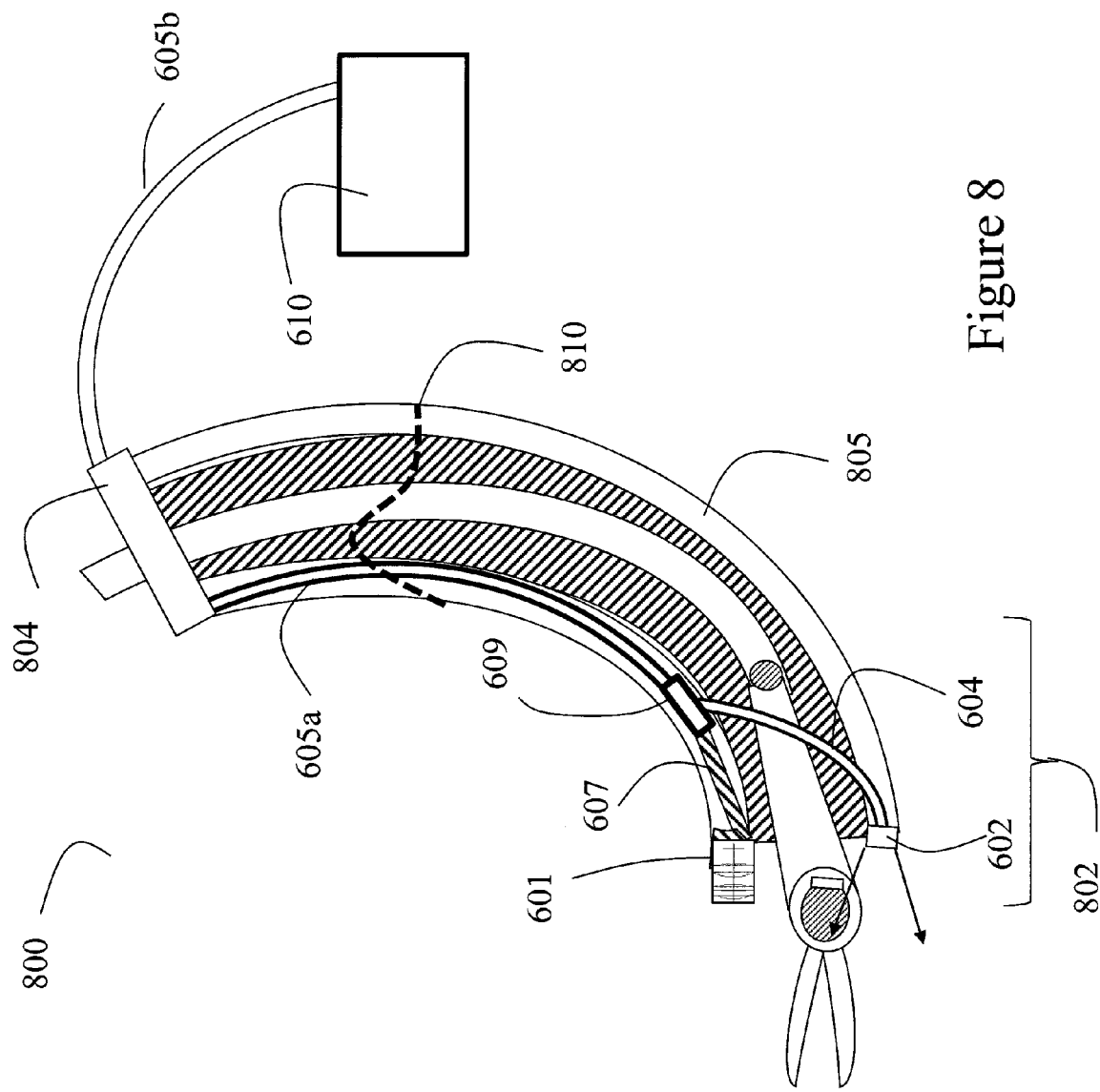
FIG. 8 illustrates another LED illumination and OE vision module (FIG. 6c) incorporated at the distal tip of a flexible, disposable catheter.

FIG. 8 illustrates an example of OE illumination and vision modules 602 and 601 installed at the distal tip 802 of a disposable flexible catheter 800 that can be inserted into a body's natural orifices. The OE illumination and vision modules 602 and 601 can be employed with catheters 800 of variable length, as represented by dashed line 810. As shown in FIG. 8, the catheter 800 includes a proximal opening 804, where flexible electronics circuit 607, electrical connection 609, flexible electrical lines 604, and 605*a* substantially running along the length, are all within the flexible catheter body 805.

Figure 9:
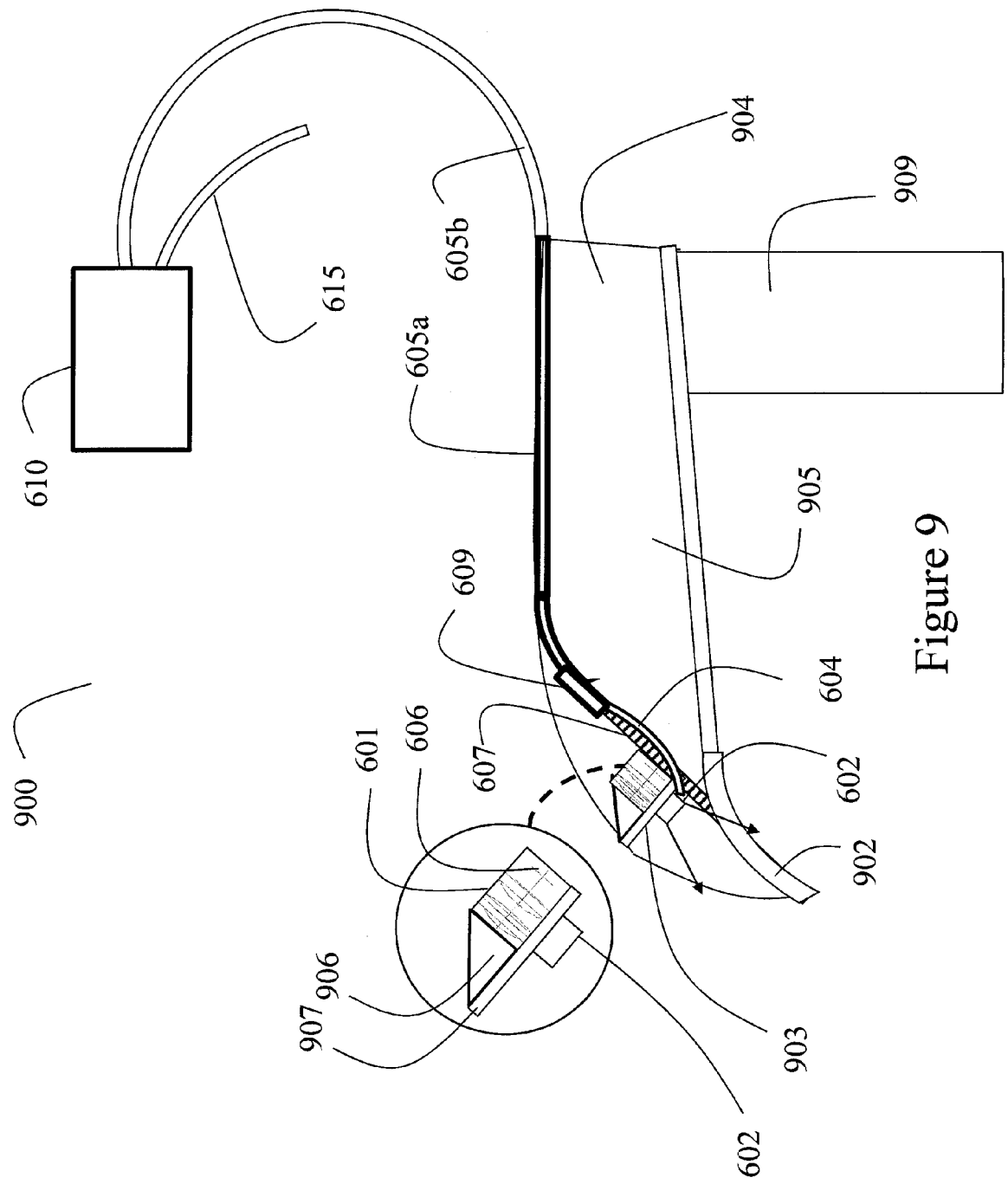
FIG. 9 illustrates an example embodiment of a completely disposable laryngoscope (including blade, handle, and connecting cable) equipped with the OE vision and illumination module of FIG. 6b.

FIG. 9 illustrates a disposable video laryngoscope 900 consisting of a handle 909, as well as a disposable cable 605*b*, that incorporates OE illumination and vision modules 602 and 601, and includes a power connection 609, drawing external power from the portable control and display 610 via a power cable 605*a,b*. The OE vision module 601 mounted on a rigid electrical board 607, is partially connected to a distal tip structure 902, with connection 609 at the opposite end of the electronic board 607, which caries power to the OE vision module 601 and illumination module 602 (see FIG. 6*b*, with the LED illumination unit 602 mounted next to the vision module 601 pointing to the tip of the laryngoscope blade), and transfers serialized image data from the image sensor 606 to USB video cable 605*a*, within the body of the laryngoscope blade 905. USB Video cable 605*a,b* additionally provides external power from the portable control and display unit 610, which may be battery operated, to the complete video laryngoscope unit consisting of the OE illumination 602 and the vision module 601.

The viewing direction of the camera module 601 can be directed and adjusted towards the tip of the laryngoscope blade by the right angle prism 906 mounted on top of the camera unit 601. The LED illuminator 602 could be mounted on small thermal pads or heat sink 907 directing the heat from the LED to around the edges of the front surface of the right angle prism 906, that acts as the window 903 to the vision module for anti-fogging. Display and Control unit 610 can electronically process the video data from the vision module

601 by flipping the image or rotating it as necessary, for correct viewing of the FOV by the user.

By incorporating the OE vision module 601 and LED illuminator 602 at the side of the distal tip of blade 905, the blade opening in proximal end 904 remains completely free for access to inside the body, for endotracheal tube insertion. For example concurrently with insertion of an endotracheal tube, the user can visualize the field indirectly using the OE vision module 601 from the side, without the inserted tube substantially hindering the examiner's view.

Removable and pluggable OE vision and illumination modules containing LED illumination can be plugged onto a variety of single use disposable or reusable, articulating and non-articulating surgical medical device bodies, used in a fixed position with respect to the medical device body, or deployed (articulated) out of the medical device body once the medical device distal end is inside the body. Through the deployment and articulation process of the OE illumination and vision modules that are plugged onto the distal tip of the medical device, the OE module can position itself outside the normal medical device volume, creating space inside the medical device and enabling further tool insertion through the cavity that the OE module was stored in during the insertion of the medical device into the body, thus allowing for further medical device functionality, or articulated to a particular position, revealing a new direction of view by the medical device (perhaps behind some body organs).

In the case of surgical procedures where delicate surgery is performed using the disposable endoscope, such pluggable OE vision and illumination systems 600 can not only be made in minimal size, but can alternately or additionally house two miniature camera systems with an extended dual USB device connection for stereoscopic view of the surgical sight, and 3D viewing for extra precision and guidance with visual depth clues.

Incorporating disposable miniature solid state OE illumination and vision modules (600) in endoscope and surgical device bodies provides a desirable cost advantage over conventional lamp and fiber guide systems, as it replaces the expensive light sources, long fiber optic light guides to transfer illumination light from the light source to the scope, and the illumination light guides inside the scope as well. Low level power is needed for the LED light sources 602, image sensors 606, and drive electronics 607. The electrical connection 609 of the OE illumination and vision module 600 is also much easier using USB type communication and power protocols, with well established mobile web camera applications in video conferencing.

Only electrical power and LED control signals need to be provided for the endoscope, eliminating the heavy and bulky fiber optics illumination cable connection to the scope, increasing the maneuverability and durability of the endoscope. OE illumination and vision modules are also more robust to shock and vibrations or extreme environmental conditions than fiber optic illumination and external camera systems.

In addition to the embodiments of FIGS. 7a-7b, and 9, articulating and/or deployable embodiments are possible for effective illumination and imaging of a surgical site. In articulating embodiments, such as the embodiment of FIGS. 10a and 10b, 11 and 12, the OE illumination and vision modules are articulated from an insertion position in which they are held within the insertion body or within a close profile of the insertion body, to an operational position where they are conveniently pointed to an object of interest. In operational position, the illumination light as well as the imaging FOV can be directed to the surgical site from beyond the endoscope body, where articulation of an OE module holding structure positions the vision module off axis from the axis of the insertion body (depicted by the dashed line 1020 in FIGS. 10b, 11, and 12), possibly increasing the functionality of the surgical device as well.

Figure 10A:
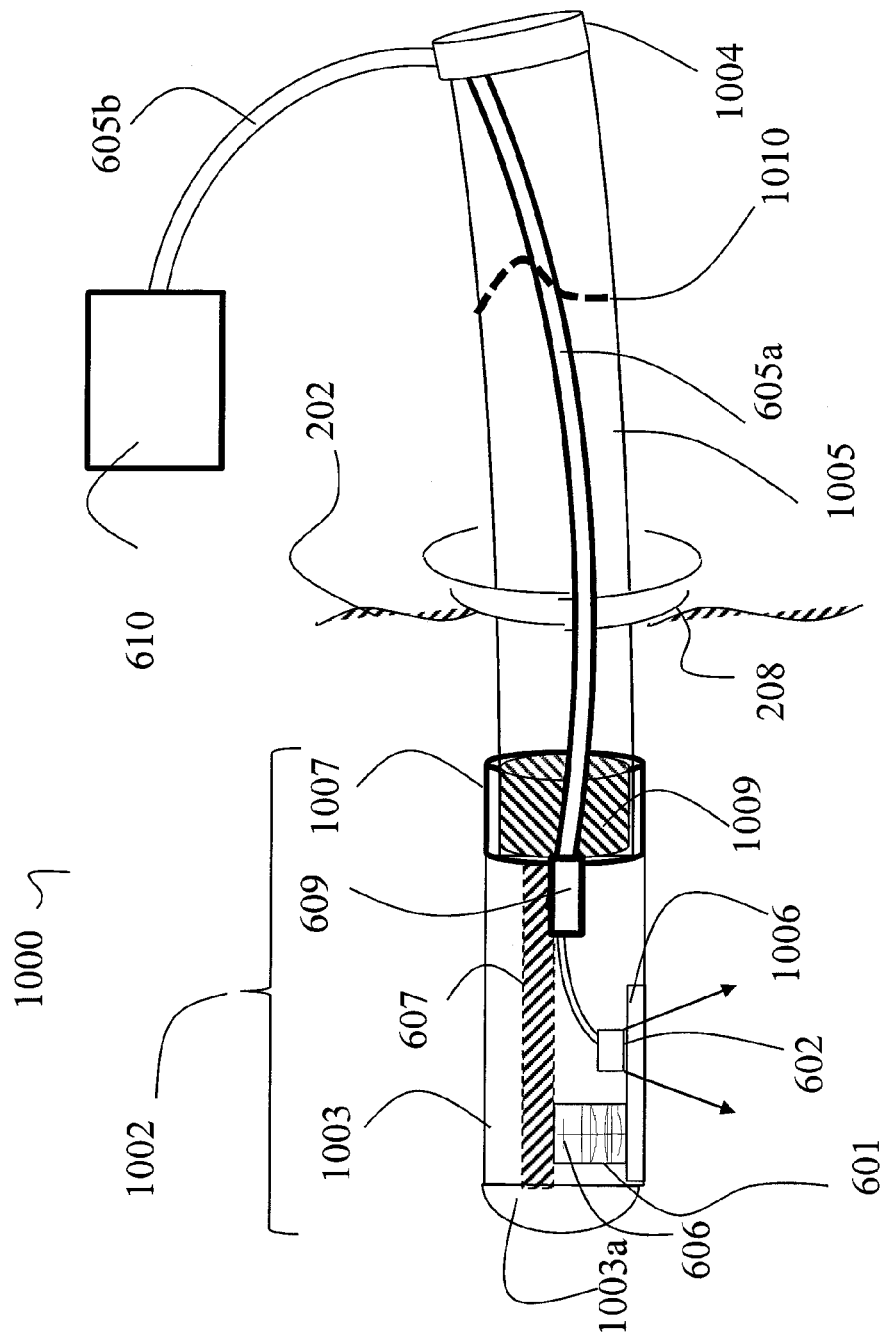
FIG. 10a illustrates an example of pluggable, and disposable OE illumination and vision module (FIG. 6b) with electrical lines running through a flexible jacket through which a medical control device can be inserted.

FIG. 10a discloses a pluggable module 1000 comprising an OE illumination 602 and vision module 601 incorporated in a single use, flexible, protective cover or jacket 1005, with a flat distal optical window 1006 sealed in the protective cover 1003, with rounded tip 1003a for easy insertion. The flexible protective cover 1005 can be made in variable lengths, denoted by the dashed lines 1010 in FIG. 10a to 12, and houses the necessary electrical connection lines 605a, to the OE illumination 602 and vision module 601 from the proximal opening 1004.

In these embodiments (FIG. 10a to 12), the protective cover 1003 and optical window 1006 are fully sealed with the optical window 1006 forming a substantially airtight seal with the protective cover 1003. Alternately or additionally, moisture can be substantially removed from within the cavity defined by the protective cover 1003 optical window 1006 such that the cavity is filed with substantially dry air. Optionally, although not shown, one or more moisture absorbing elements (beads) can be disposed within the cavity defined by the protective cover 1003 and optical window 1006 to maintain the air within the cavity substantially devoid of moisture.

Figure 10B:
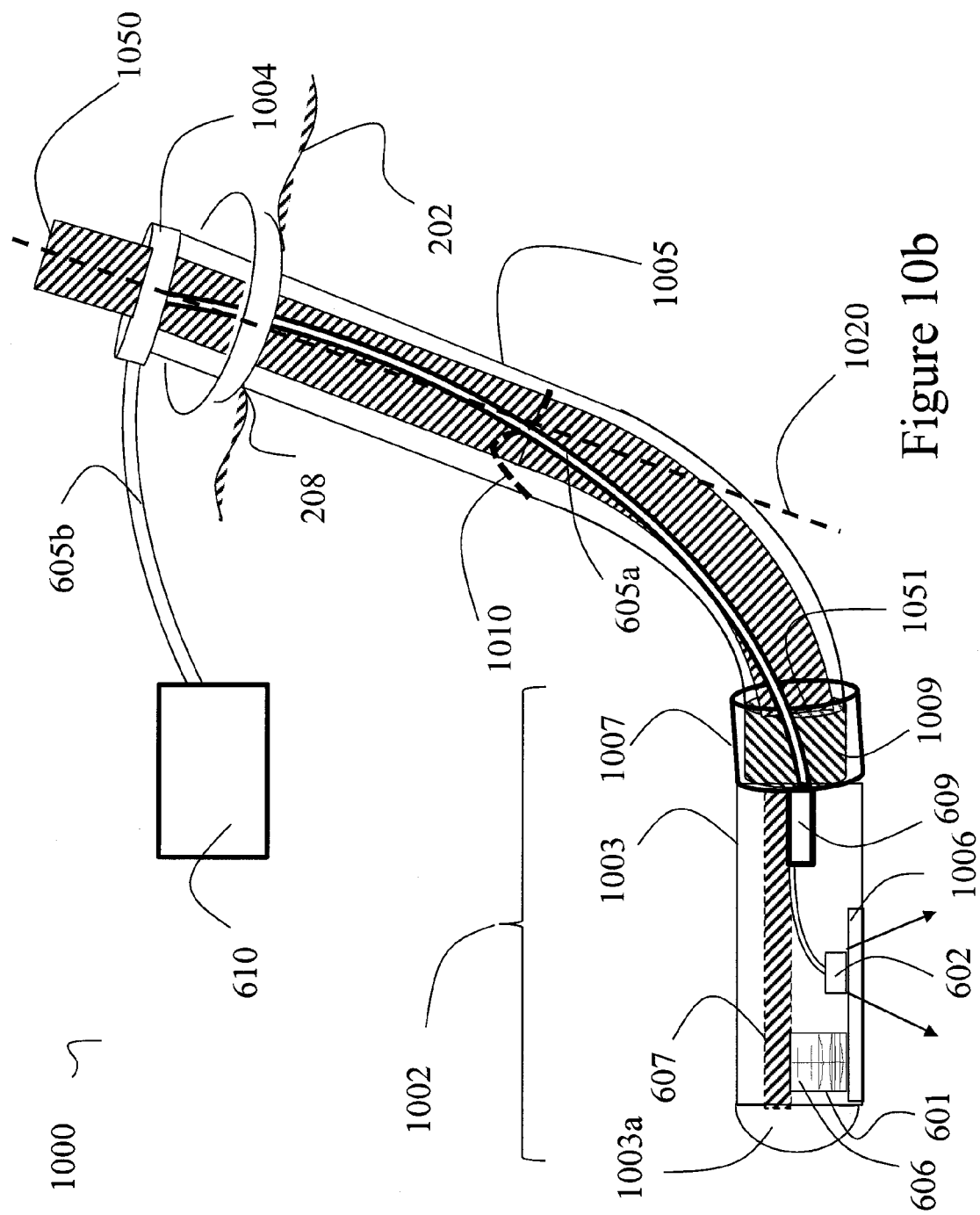
Figure 11:
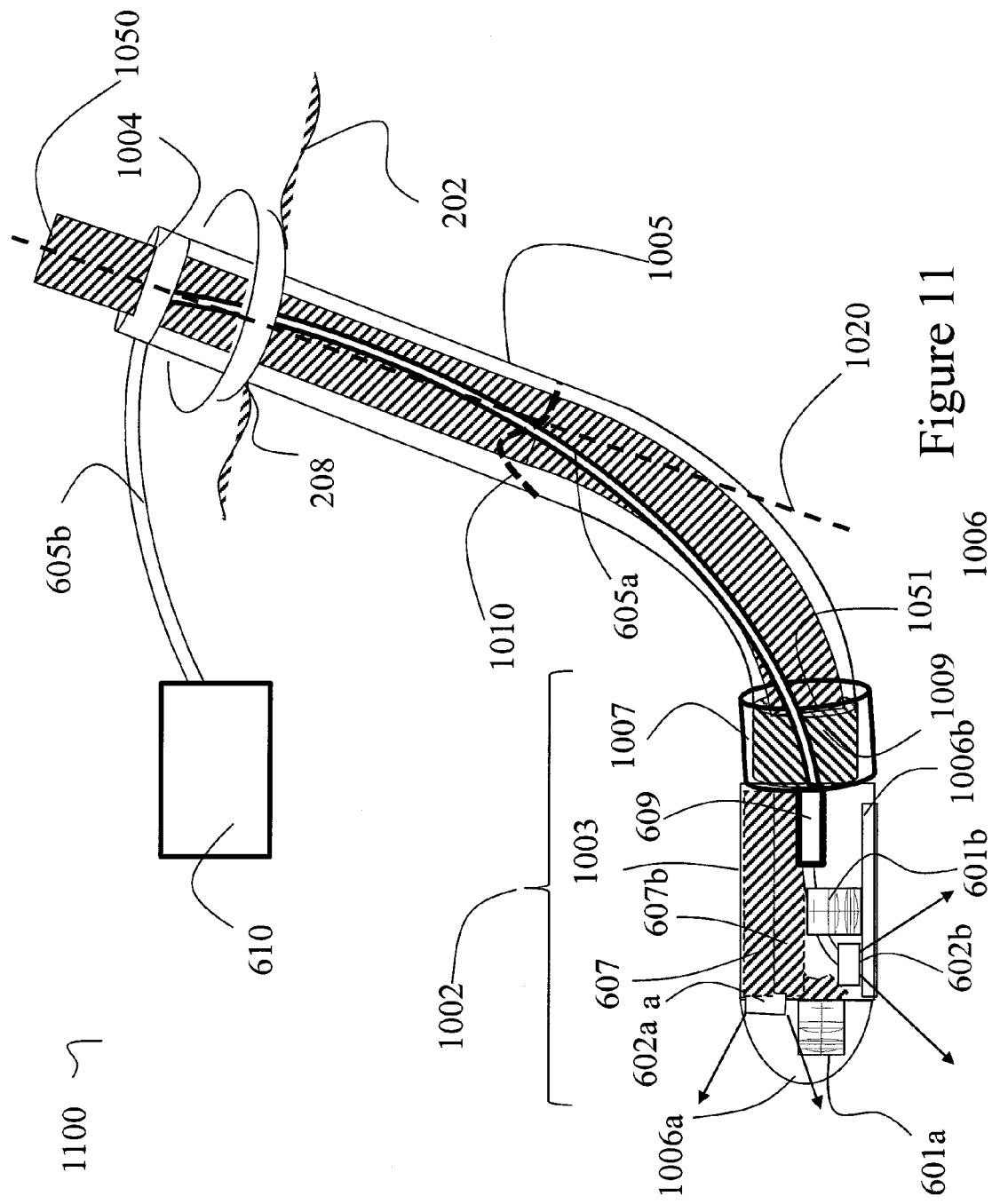
FIG. 11 illustrates the pluggable and disposable device of FIG. 10a-10b, with dual OE illumination and vision modules of FIGS. 6a and 6b, together providing Hyper, or extended FOV (Field Of View).
Figure 12:
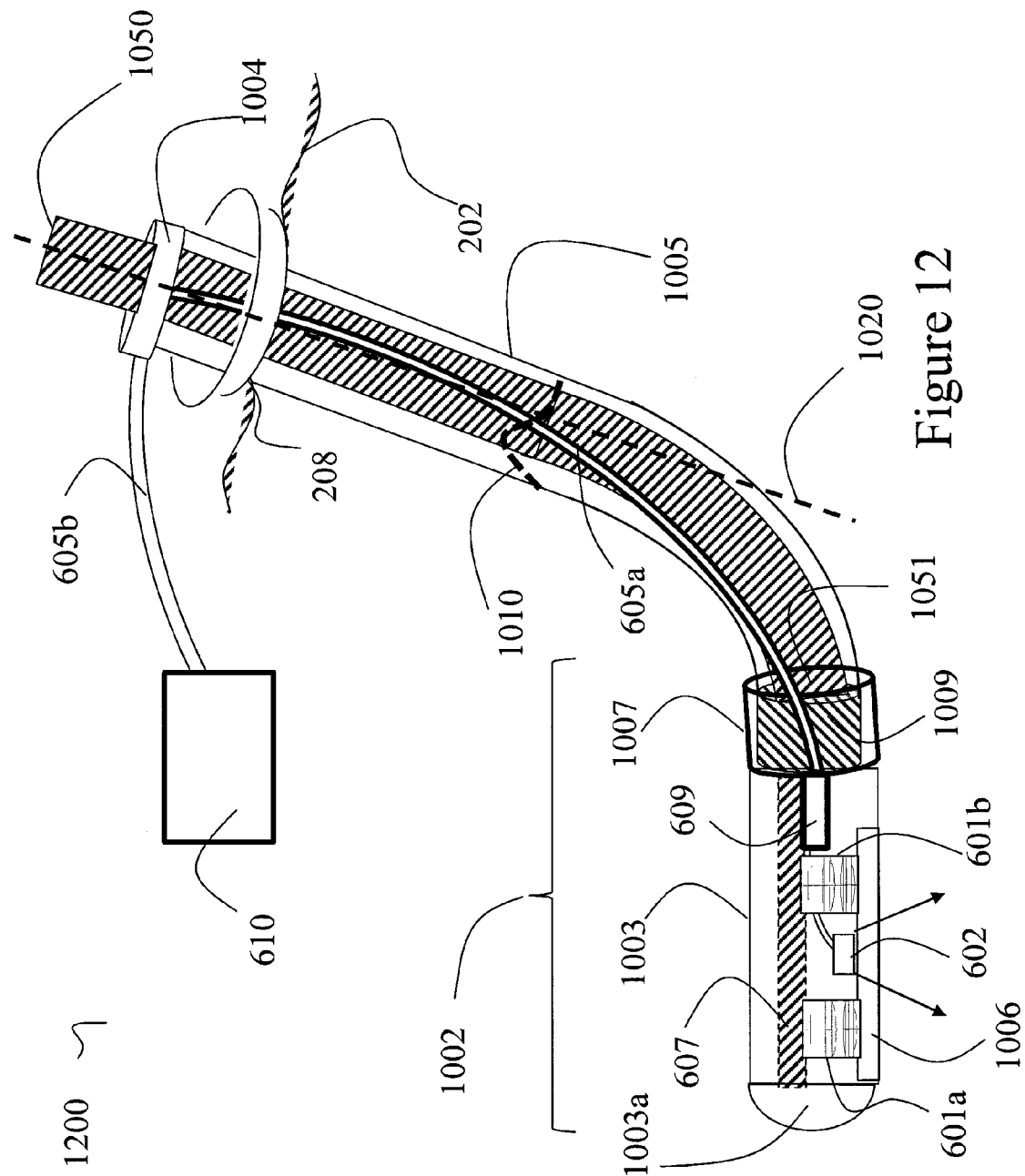
FIG. 12 illustrates a dual camera version of OE illumination and vision module of FIG. 6a, housed in the pluggable and disposable device of FIGS. 10a and 10b, providing stereoscopic vision endoscope.

In these embodiments (FIG. 10a to 12), the flexible body 1005 includes a proximal opening 1004 operable to receive a body 1050 therein. For example, FIGS. 10b, 11 and 12, represent the insertion of the body 1050 into the flexible body 1005 of the pluggable module 1000, 1100, and 1200. The body 1050 can be rigid, flexible, formed, or articulating. The body 1050 and pluggable module 1000, 1100, and 1200 form a curved, flexible, or articulating disposable endoscope. When the body 1050 comprises an articulating device, appropriate mechanical connection can be made between a base 1009 of the rigid tip 1002 of the pluggable module 1000, 1100 and 1200, and a distal reference surface 1051 of the body 1050 to allow full one-to-one articulation of the pluggable module 1000, 1100, 1200, with the body 1150 at the distal tip. The flexible hollow body of the disposable endoscope 1000, can have separate tightening means 1007, at the connection base 1009, to grab and lock onto the articulating device tip 1050 (1051 surface). Such articulating device acts as a Variable FOV endoscope by means of articulation, imaging different areas inside the body.

The portable control and display unit 610 is connected to the pluggable module 1000, 1100, and 1200, using electrical cable 605b, which extends as electrical cable 605a to the electrical connection 609 of the electronic circuit board 607 of the OE vision and illumination module near distal end, within the flexible jacket 1005. The vision module 601 in FIGS. 10a and 10b, sits on a rigid electrical board 607, and along with the illuminator 602 receives power from the electrical connection 609 (as depicted in FIG. 6b), which could be made to run as a USB device. LED illuminator 602 is mounted on or near window 1006, for efficient heat transfer from the LED to the window as anti-fogging means. Alternatively a passive resistor could be mounted on the window to act as de-fogging unit, when the device is used inside the body with higher temperature than outside.

Multiple color LEDs can be used within the tip housing 1003 of the disposable endoscope 1000, where the display and control unit 610 synchronizes the on/off timing of each color LED with the frame rates of a black and white camera sensor 606. Such disposable endoscope could be used for spectral imaging with narrow band LED light output in the illuminator module, or with wider wavelength band illumination in the visible range time synchronized with a black and white image sensor 606, to provide full color vision where each color frame takes advantage of the full resolution of the image sensor 606.

In alternate embodiments of all of the pluggable OE illumination and vision modules in the form of cannulas, catheters, and other devices described above that use LEDs for illumination, Solid State Laser Diodes (LD) or VSCELs can alternately or additionally be employed within the OE illumination and vision module or independently at the distal end of pluggable single use devices. For instance, Infrared (IR) Imaging employs IR solid state light sources to illuminate intra-vein or close tissue diagnostic and surgical procedures. IR detectors and special image sensors with modified optical filters in front of their pixels can be employed within OE vision modules for through tissue and blood imaging along with infrared light sources that have appreciable penetration depth in human tissue, blood or other bodily fluids, such as urine. Using a high intensity IR source at the surgical or examination site with control over the intensity, radiation pattern, and the direction of illumination can help with critical surgical procedures inside the vein, heart and other body organs.

By placing the illumination light sources at close proximity to the object inside the body in diagnostic or surgical procedures, the losses in conjunction with the transmission of light from the external source to the surgical site are eliminated. Thus, light sources that have equal efficiency in converting electrical power to useful light, can be operated in much lower input power, eliminating the need for sophisticated power and heat management. Power and control signals transmitting through appropriate wires and flex circuitry, can be easily routed along the tool or endoscope body to the light source and OE vision module.

In some embodiments of the invention, multiple OE vision modules 601 are employed within a single pluggable module to obtain a combined hyper or extended field of view of an imaging site. FIG. 11 illustrates such device, where the front vision module camera 601*a*, and LED illumination 602*a* are behind a common bulb type window 1006*a*, while the side view is obtained from a second camera 601*b* illuminated mostly by LED illuminator 602*b*, through the flat window 1006*b* of disposable endoscope. Alternately or additionally, inputs from two cameras 601*a* and 601*b* pointing in the same direction of view, can be obtained for stereoscopic viewing in a disposable stereoscopic endoscope 1200, as illustrated in FIG. 12. In these and other embodiments, the portable control and display unit 610 can be used to house all the control electronics and software necessary to power the OE vision module(s) 601, control illumination and imaging functionality of illumnation module(s) 602, data transmission control (using standard network device protocol such as a in a USB host driving one or more web cameras with on board illumination), as well as any image processing and/or display functionalities. For instance, the portable control and display unit 610 can include illumination and imaging control electronics that provide illumination and/or imaging control of multiple OE illumination modules 602 and/or the OE vision modules 601. Alternately or additionally, the portable control and display unit 610 can include image processing electronics that provide image processing of image data received from multiple OE vision modules 601.

The portable control and display unit 610 can be a portable display unit used in a fixed position in a medical facility, or as a mobile application with an LCD, plasma, or other display unit capable of displaying 2D or 3D (stereoscopic) images. The portable control and display unit 610 can alternately or additionally be worn by a user, with a wired or wireless connection to the input devices (e.g., the OE vision module(s) 600), where the user can observe 2D or 3D stereo images and video conveniently by looking at the display mounted on an arm of the user, hanging from a neck of the user, or otherwise mounted (clipped on) to the user.

The portable control and display unit 610 can be electrically powered using a power cable, or use rechargeable or disposable batteries. In all the embodiments, the electrical power supply of the portable control and display unit 610, whether from a power cable or battery, provides power for the portable control and display unit 610 as well as the OE illumination and vision modules 602, 601 to which the portable control and display unit 610 is attached via cable 605*a*,*b*. Single or multiple OE illumination 602 and vision modules 601 can be connected to the portable control and display unit 610, which portable control and display unit 610 can be configured to provide synchronized control of complete illumination and image capture. The portable control and display unit 610 could also provide means for local and transferable means of image and video storage, with magnetic and/or electrical storage devices within its housing. A user interface can be provided on the portable control and display unit 610 and may include hard or soft electronic keys, a mouse or joystick, a touch screen, and/or voice activated command electronics. The user interface can be employed to adjust, control, display, process, transfer, store or retrieve the image and video data. The portable control and display unit 610 can alternately or additionally comprise a multifunctional unit that is used as both a general portable medical display and one or more of: a cell phone, a mini computer with wireless capabilities, a GPS unit, a personal digital assistant (PDA), a note-taking device, a dictation device, a video conferencing device, or the like.

The user interface devices described above, including hard or soft electronic keys, a mouse or joystick, a touch screen, and voice activated command electronics all serve as examples of input and/or output means that can be included in the portable control and display unit 610. The portable control and display unit 610 can alternately or additionally include computing means, such as a processor, microprocessor, controller, or the like. Alternately or additionally, the portable control and display unit 610 can include cellular communication capabilities and/or wireless connectivity.

Figure 13A:
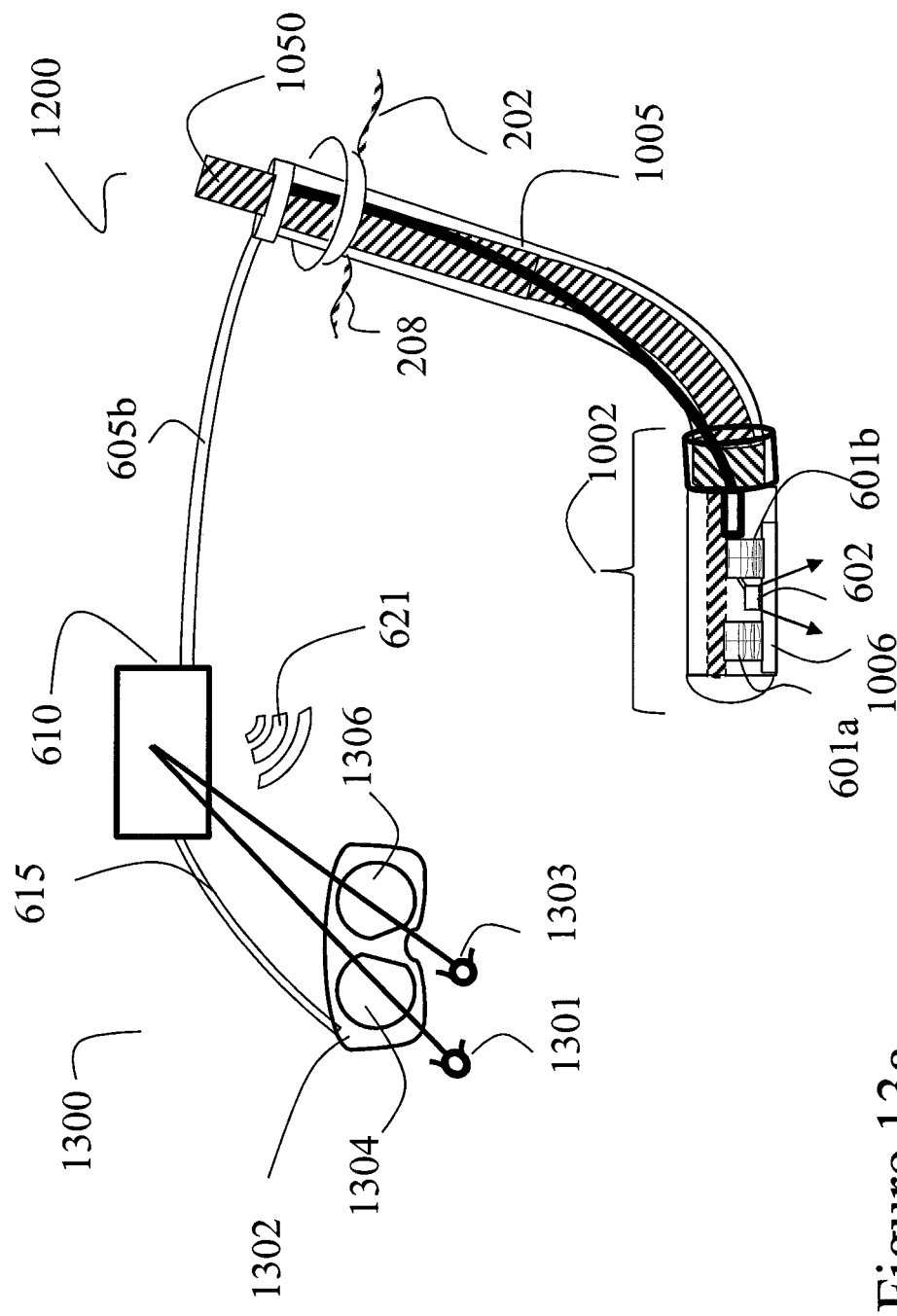
FIGS. 13a-13b, illustrate 3D viewing mechanisms for the stereoscopic disposable endoscope of FIG. 12.

In some embodiments that include stereoscopic or 3D image capture 1200, as illustrated in FIG. 13*a*, the portable control and display unit 610 can display time-synchronized alternate left and right frames of the video from the medical device vision modules 601*a* and 601*b*, where a pair of time-synchronized liquid crystal shutters, 1304 and 1306, in front of the user's left and right eyes (1301 and 1303), allow each eye to see the corresponding alternating stereoscopic images. In such embodiments, the user can wear 3D-viewing time-synchronized shutter glasses 1300, with frame 1302 depicted in FIG. 13*a*, while viewing the 3D displayed data on the portable control and display unit 610, while the 3D-viewing liquid crystal shutter glasses are time-synchronized with the portable control and display unit 610 via a timing signal received via wireless interface 621 (e.g., IR connection, Bluetooth) or hardwired connection 615, to the portable control and display unit 610.

Figure 13B:
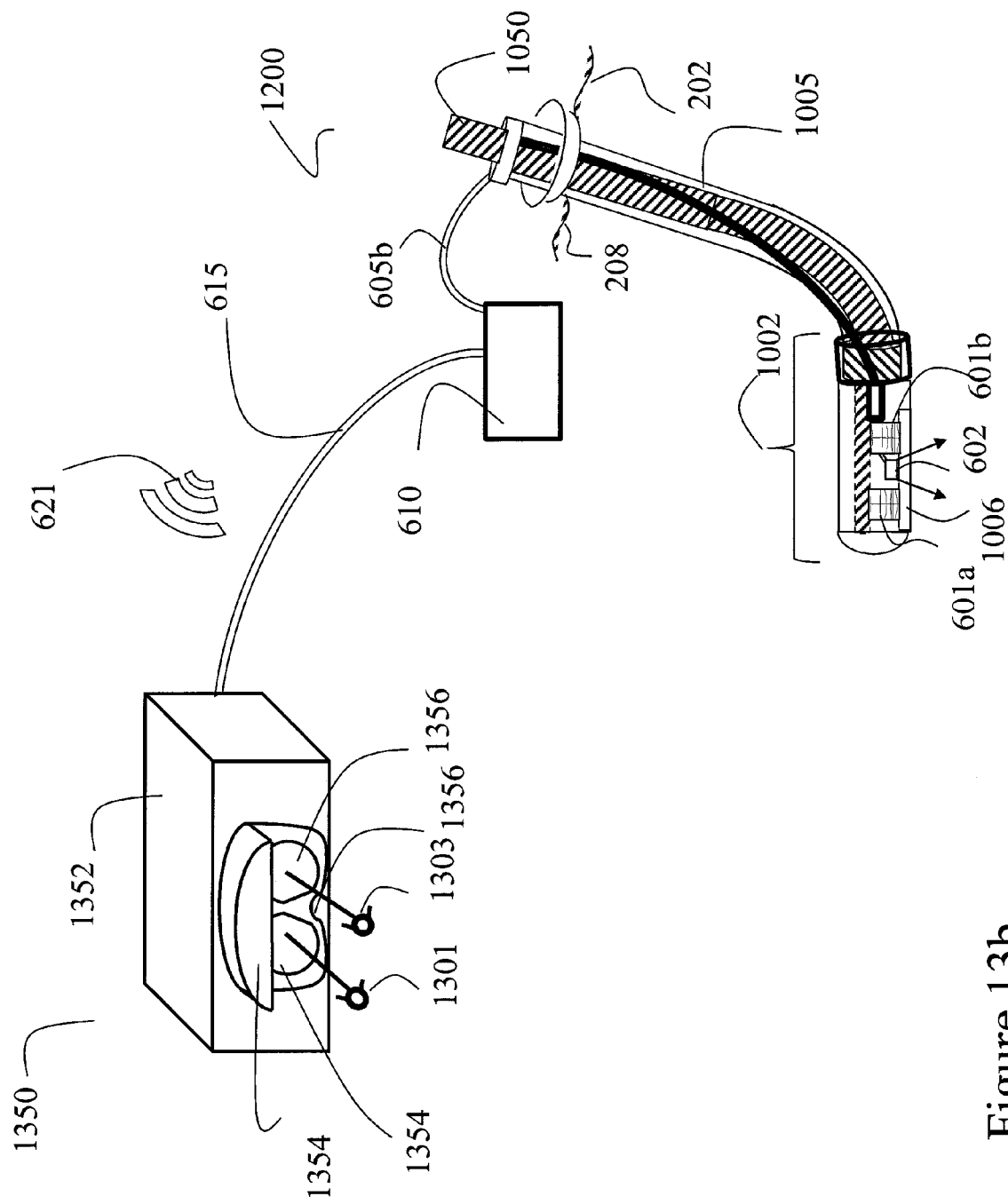

An independent 3D viewer illustrated in FIG. 13*b* with its' own left and right LCDs for stereoscopic viewing (or time synchronized left and right image on single LCD, similar to the display unit 610 in FIG. 13*a*, with left and right liquid crystal shutters 1354 and 1356) could be used alternatively to view the 3D video from the disposable stereo endoscope 1200. In which case the control and display unit 610 could be displaying the 2D images from either left of right vision modules 601*a* or 601*b*, while relaying the 3D video data to the 3D viewer 1350 through wired or wireless connections 621 and 615. The independent 3D viewer could be equipped with headrest 1354 and nose relief 1356 on its housing 1352.

The portable control and display unit 610 may comprise a flat panel LCD screen, plasma screen, or other suitable screen such as organic LED display. A separate sterile disposable cover could be draping the portable control and display unit, preserving all user interface and electrical connection functionalities. Alternately or additionally, the portable control and display unit 610, or it's separate sterile cover can have multiple positioning and attachment possibilities, depending on its size, the type of medical device it's used with, the type of medical procedure, the location the procedure is performed, and the type of user interface necessary. In fixed office or surgical environments, the portable control and display unit 610 can be fixed to a wall, mounted on an IV post, clipped onto as patient cover or drape, or can be hung from a frame structure, with tilt and rotation capabilities and in a removable and portable form. Alternately or additionally, a fixed control and display unit can be employed to control OE illumination and vision modules 602 and 601 and/or to display image data captured by OE vision modules 600.

FIGS. 14*a*-14*c*, illustrate "wearable" configurations of the portable control and display unit 610 where the portable control and display unit 610 is attached to the arm or wrist of a user via a wearable attachment device. In more detail, FIG. 14*a* illustrates a wearable attachment device comprising a resiliently deformable bracelet 1402, such as a memory shaped bracelet. The bracelet 1402 can be unfolded to prepare for use, and then snapped to take it's round shape (dictated by the memory shaped strip inside the bracelet 1402) around the user's arm or wrist.

FIG. 14*b* illustrates a wearable attachment device comprising a wide elastic band and Velcro strip 1404 that acts as a cover to the bracelet 1402. As illustrated in FIG. 14*b*, the Velcro strip 1404 can be employed for adjustable attachment or wearing of the portable control and display unit 610 on the arm or the wrist of the user, as its' Velcro strip grabs onto the back surface of the display and control unit 610 or its' secondary disposable sterile protective cover, that is equipped with mating Velcro, at the interface 1401.

The convenient and flexible Velcro based wearable attachment device of FIGS. 14*a* and 14*b*, can be adjusted using the adjustable Velcro mounting, to allow convenient direct viewing of the display by the user during use, on the user's arm 1403 (FIG. 14*c*). The wearable attachment devices of FIGS. 14*a*-14*c* can be worn over a user's clothing during or before use, with or without physical connection to the OE vision modules 600 or other input devices.

Alternately or additionally, as shown in FIG. 14*c*, the wearable attachment devices of FIGS. 14*a* and 14*b*, or other wearable attachment devices, can include an additional protective and shielding mechanism 1406. The protective and shielding mechanism 1406 can be unfolded from the surface of portable control and display unit 610 to prevent glare on the portable control and display unit 610 when used in the outdoors or other environments. The portable control and display units 610 employed in conjunction with the wearable attachment devices of FIGS. 14*a*-14*c*, and/or in conjunction with other wearable attachment devices, can contain various image processing, storage, and wireless communication capabilities and can be powered independently by rechargeable batteries, as already explained above.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A device for insertion into an anatomical cavity, the device comprising:
    a disposable body having a proximal section and a distal section, the distal section configured to be at least partially inserted into the anatomical cavity; and
    an opto-electronic module functionally positioned on the distal section of the body, the opto-electronic module including:
        a digital image sensor positioned at the distal section of the body, the digital image sensor configured to output digital video signals including parallel digital video signals or MIPI serialized digital video signals,
        an illuminator positioned at the distal section of the body,
        a circuit board conductively coupled to the digital image sensor, the circuit board configured to be at least partially inserted into the anatomical cavity, the circuit board further configured to convert the digital video signals output by the digital image sensor to Universal Serial Bus Video Class (UVC) video signals,
        electrical lines conductively coupled to the circuit board such that the electrical lines are conductively coupled to the digital image sensor and the illuminator, the electrical lines functionally coupled to the body from the circuit board to the proximal section of the body, the electrical lines including an electrical cable having a first end and a second end, the first end functionally coupled to the proximal section of the body, and
        a Universal Serial Bus (USB) connector conductively coupled to the second end of the electrical cable, the USB connector configured to electrically connect the electrical lines to a control unit configured to control the digital image sensor as a USB camera device, the USB connector further configured to communicate the UVC video signals to the control unit.

2. The device of claim 1, wherein the digital image sensor includes a digital charge-coupled device (CCD) sensor or a digital complementary metal-oxide-semiconductor (CMOS) sensor.

3. The device of claim 1, wherein the illuminator includes a light emitting device (LED), a laser diode (LD), an ultraviolet (UV) light source, or an infrared (IR) light source.

4. The device of claim 1, wherein the circuit board is further configured to distribute power from the electrical lines to the illuminator and the digital image sensor.

5. The device of claim 1, wherein the circuit board is further configured to receive the MIPI-enabled serialized digital sensor output transmitted to the circuit board through the flexible electrical lines, convert the MIPI-enabled serialized digital sensor output to UVC digital video format, and directly communicate the UVC digital video to a portable display and controller unit including the control unit.

6. The device of claim 1, wherein the body and the opto-electronic module are configured to form a cannula including a tool access within the body.

7. The device of claim 6, wherein the distal end includes a distal tip configured to be expanded radially when the distal end is at least partially inserted into the anatomical cavity.

8. The device of claim 7, wherein the image sensor and the illuminator are located on the distal tip such that the image sensor and the illuminator are expanded radially when the distal tip is expanded radially.

9. The device of claim 1, wherein the body is one or more of: rigid, partially rigid, flexible, partially flexible, filled inside, or hollow inside.

10. The device of claim 1, wherein the device comprises a catheter with a tool access hole inside the device.

11. The device of claim 1, wherein the device body is a laryngoscope blade.

12. The device of claim 11, wherein the opto-electronic vision module direction of view is directed towards the tip of the laryngoscope blade using optical components such as mirrors or prisms.

13. The device of claim 1, wherein the opto-electronic module is configured to be removably attached to the body.

14. The device of claim 1, wherein the opto-electronic module is positioned in a dry air filled housing located on the distal end of the body, the digital image sensor and the illuminator positioned behind an airtight optical window.

15. The device of claim 14, wherein the dry air filled housing includes one or more moisture absorbing elements to keep the air dry.

16. The device of claim 14, wherein multiple opto-electronic vision modules and illuminators are housed within the sealed distal tip housing, behind a window or multiple windows.

17. The device of claim 16, wherein dual vision modules directed at the same FOV, provide stereoscopic view of the site.

18. A device for insertion into an anatomical cavity, the device comprising:
   a disposable body including:
      a proximal section,
      a distal section configured to be at least partially inserted into the anatomical cavity, and
      an opening configured to allow a medical tool to be inserted through at least a portion of the body and into the anatomical cavity; and
   an opto-electronic module located on the distal section of the body, the opto-electronic module including:
      a first digital image sensor located on the distal section of the body, the first digital image sensor configured to output parallel digital video signals or MIPI serialized digital video signals,
      an illuminator located on the distal section of the body,
      a circuit board conductively coupled to the first digital image sensor, the circuit board configured to be at least partially inserted into the anatomical cavity, the circuit board further configured to convert the digital video signals output by the first digital image sensor to Universal Serial Bus Video Class (UVC) video signals,
      flexible electrical lines conductively coupled to the circuit board, the flexible electrical lines located on the body from the circuit board to the proximal end of the body, the flexible electrical lines including an electrical cable having a first end and a second end, the first end functionally coupled to the proximal end of the body, and
      a Universal Serial Bus (USB) connector conductively coupled to the second end of the electrical cable, the USB connector configured to electrically connect the flexible electrical lines to a control unit configured to control the first digital image sensor as a USB camera device, the USB connector further configured to communicate the UVC video signals to the control unit.

19. The device of claim 18, wherein the medical tool is rigid, flexible, articulating, robotic, or configured to deliver suction, irrigation, biomedical agents, medication, or medical devices to the anatomical cavity.

20. The device of claim 19, wherein the opto-electronic module is articulated by the medical access device, configured such that in an insertion position, the opto-electronic module is substantially contained within a profile of the device body, and in a articulated position, at least a portion of the opto-electronic module is disposed external to the profile of the device body, as the direction of view is adjusted according to use.

21. The device of claim 18, wherein the body is configured to lock the medical tool into place with respect to the opto-electronic module.

22. The device of claim 18, wherein the body further includes an imaging window interposed between the distal end and the image sensor, wherein the illuminator or a heat-generating resistor of the opto-electronic module is configured such that heat from the illuminator or the heat-generating resistor substantially prevents formation of condensation on the imaging window.

23. The device of claim 18, wherein the opto-electronic module further includes a second digital image sensor, the first digital image sensor directed at a first field of view (FOV) and the second digital image sensor directed at a second FOV such that the first FOV and the second FOV are configured to be combined to provide an Extended or Stereoscopic FOV.

24. The device of claim 23, wherein the second digital image sensor is configured to be controlled by the control unit.

25. The device of claim 24, wherein the control unit is further configured to control the second digital image sensor as a USB device.

* * * * *